United States Patent
Kosiorek et al.

(10) Patent No.: US 12,349,924 B2
(45) Date of Patent: Jul. 8, 2025

(54) MECHANICAL TOURNIQUET APPARATUS AND METHOD OF USE

(71) Applicant: ALPHAPOINTE, Kansas City, MO (US)

(72) Inventors: Christopher B. Kosiorek, La Vernia, TX (US); Ryan Williams, Olathe, KS (US); Esra Abir, New York, NY (US); Brenda Mee, West Newfield, ME (US); Dexter C. Drayton, San Antonio, TX (US); Neslihan Damar, Instanbul (TR); Nilufer Polat, Brooklyn, NY (US); Yavuz Avci, Sunnyside, NY (US)

(73) Assignee: ALPHAPOINTE, Kansas City, MO (US)

( * ) Notice: Subject to any disclaimer, the term of this patent is extended or adjusted under 35 U.S.C. 154(b) by 491 days.

(21) Appl. No.: 17/740,082

(22) Filed: May 9, 2022

(65) Prior Publication Data
US 2022/0265281 A1    Aug. 25, 2022

Related U.S. Application Data

(60) Continuation-in-part of application No. 16/790,536, filed on Feb. 13, 2020, now Pat. No. 11,504,135, and (Continued)

(51) Int. Cl.
A61B 17/135    (2006.01)
A61B 17/00    (2006.01)
(Continued)

(52) U.S. Cl.
CPC .. *A61B 17/135* (2013.01); *A61B 2017/00526* (2013.01); *A61B 2017/00544* (2013.01); (Continued)

(58) Field of Classification Search
CPC .............. A61B 17/132; A61B 17/1322; A61B 17/1325; A61B 17/1327; A61B 17/135; A61B 17/1355
See application file for complete search history.

(56) References Cited

U.S. PATENT DOCUMENTS

| | | |
|---|---|---|
| 1,406,770 A | 2/1922 | Smith |
| 2,084,212 A | 6/1937 | Moreira |
| | (Continued) | |

FOREIGN PATENT DOCUMENTS

| | | |
|---|---|---|
| AU | 2014324601 B2 | 4/2015 |
| AU | 2014324601 A1 | 5/2016 |
| | (Continued) | |

OTHER PUBLICATIONS

"Abdominal Aortic Tourniquet, http://www.militarytimes.com/article/20130928/NEWS/309280006/Abdominal-tourniquet-gives-lifesaving-time, accessed Oct. 28, 2014.", Oct. 28, 2014.
(Continued)

*Primary Examiner* — Todd J Scherbel
(74) *Attorney, Agent, or Firm* — Kutak Rock LLP; Brian L. Main

(57) ABSTRACT

A pre-fabricated tourniquet that is easy to apply, that ensures consistent and even circumferential pressure, that is lightweight, that provides standard life saving operation, and that can be utilized in any setting or situation, and related methods are provided. Mechanically constricting tourniquet apparatus and related methods are provided that are comprised of a tourniquet body, a carriage, a torsion bar, a receiver, and a slider. The tourniquet is long enough to encircle a human limb, for example, an arm or leg. The tourniquet apparatus includes several features for preventing or otherwise limiting harm to users and/or damage to the tourniquet apparatus itself.

10 Claims, 10 Drawing Sheets

Related U.S. Application Data a continuation-in-part of application No. 16/369,902, filed on Mar. 29, 2019, now Pat. No. 11,324,516, said application No. 16/790,536 is a continuation-in-part of application No. 15/847,033, filed on Dec. 19, 2017, now Pat. No. 10,716,577, said application No. 16/369,902 is a division of application No. 14/500,191, filed on Sep. 29, 2014, now Pat. No. 10,271,855, which is a continuation of application No. 14/500,084, filed on Sep. 29, 2014, now Pat. No. 9,855,055.

(60) Provisional application No. 62/805,753, filed on Feb. 14, 2019, provisional application No. 61/883,769, filed on Sep. 27, 2013, provisional application No. 61/883,797, filed on Sep. 27, 2013.

(51) Int. Cl.
*A61B 17/132* (2006.01)
*A61B 90/90* (2016.01)

(52) U.S. Cl.
CPC ........... *A61B 17/1327* (2013.01); *A61B 90/90* (2016.02); *Y10T 29/49826* (2015.01)

(56) References Cited

U.S. PATENT DOCUMENTS

| | | |
|---|---|---|
| 2,084,412 A | 6/1937 | Schaefer |
| 2,387,428 A | 10/1945 | Brothers |
| 2,410,880 A | 11/1946 | Hennicke |
| 2,528,078 A | 10/1950 | Quilter |
| 2,702,551 A | 2/1955 | Hobson et al. |
| 2,754,825 A | 7/1956 | Richmond |
| 2,841,149 A | 7/1958 | Marsden |
| 2,893,394 A | 7/1959 | Thomsen |
| 3,120,846 A | 2/1964 | Fletcher |
| 3,165,803 A | 1/1965 | Gaylord |
| 3,492,995 A | 2/1970 | Ceravolo |
| 3,910,280 A | 10/1975 | Talonn |
| 4,102,343 A | 7/1978 | Schneider |
| 4,125,115 A | 11/1978 | Mayo et al. |
| 4,149,540 A | 4/1979 | Hasslinger |
| 4,273,130 A | 6/1981 | Simpson |
| 4,279,367 A | 7/1981 | Jacobs |
| 4,501,027 A | 2/1985 | Olsson |
| 4,516,576 A | 5/1985 | Kirchner |
| 4,640,281 A | 2/1987 | Sturm et al. |
| 4,724,829 A | 2/1988 | Knapps |
| 4,911,162 A | 3/1990 | Wolff |
| 5,295,996 A | 3/1994 | Blair |
| 5,304,202 A | 4/1994 | Stahl |
| 5,312,350 A | 5/1994 | Jacobs |
| 5,314,437 A | 5/1994 | Holtsch |
| 5,372,575 A | 12/1994 | Sebastian |
| 5,413,582 A | 5/1995 | Eaton |
| 5,451,234 A | 9/1995 | Wassermann |
| 5,607,448 A | 3/1997 | Stahl et al. |
| 5,649,954 A | 7/1997 | McEwen |
| 5,690,672 A | 11/1997 | Cohen |
| 5,893,870 A | 4/1999 | Talen et al. |
| 6,053,169 A | 4/2000 | Hunt |
| 6,131,972 A | 10/2000 | Whitehead et al. |
| 6,682,547 B2 | 1/2004 | McEwen et al. |
| 6,746,470 B2 | 6/2004 | McEwen et al. |
| 6,833,001 B1 | 12/2004 | Chao |
| 6,884,254 B2 | 4/2005 | Brooks |
| 6,899,720 B1 | 5/2005 | McMillan |
| 6,960,023 B2 | 11/2005 | Hsu et al. |
| 6,960,223 B1 | 11/2005 | Ambach |
| 7,468,067 B2 | 12/2008 | Licata et al. |
| 7,582,102 B2 | 9/2009 | Heinz et al. |
| 7,604,651 B1 | 10/2009 | Harris et al. |
| 7,776,064 B2 | 8/2010 | Jennifer et al. |
| 7,842,067 B2 | 11/2010 | Esposito |
| 7,892,253 B2 | 2/2011 | Esposito et al. |
| D649,642 S | 11/2011 | Johnson |
| 8,047,850 B2 | 11/2011 | Esposito et al. |
| 8,303,620 B2 | 11/2012 | Johnson et al. |
| 8,343,182 B2 | 1/2013 | Kirkham |
| 8,348,970 B2 | 1/2013 | Janota |
| 8,425,551 B2 | 4/2013 | McEwen et al. |
| 8,486,106 B2 | 7/2013 | Warburton |
| 8,568,341 B2 | 10/2013 | Flood |
| 8,707,468 B2 | 4/2014 | Reynolds et al. |
| 8,834,517 B2 | 9/2014 | Croushorn et al. |
| 8,863,333 B2 | 10/2014 | Cain et al. |
| 8,926,651 B2 | 1/2015 | McDonald et al. |
| 9,855,055 B2 | 1/2018 | Kosiorek et al. |
| 10,271,855 B2 | 4/2019 | Kosiorek et al. |
| 10,278,708 B2 | 5/2019 | Demas et al. |
| 10,716,577 B2 | 7/2020 | Kosiorek et al. |
| 11,324,516 B2 | 5/2022 | Kosiorek et al. |
| 11,504,135 B2 | 11/2022 | Kosiorek et al. |
| 2003/0028215 A1 | 2/2003 | Brooks |
| 2003/0139766 A1 | 7/2003 | McEwen et al. |
| 2004/0226150 A1 | 11/2004 | Beletsky |
| 2005/0240217 A1 | 10/2005 | Jennifer et al. |
| 2005/0267518 A1 | 12/2005 | Wright et al. |
| 2005/0273134 A1 | 12/2005 | Esposito |
| 2006/0095072 A1 | 5/2006 | Tenbrink et al. |
| 2006/0281611 A1 | 12/2006 | Sato |
| 2007/0038243 A1 | 2/2007 | Rutherford |
| 2007/0185428 A1 | 8/2007 | Harder |
| 2007/0250109 A1 | 10/2007 | Kerstein et al. |
| 2008/0183207 A1 | 7/2008 | Horne |
| 2008/0209650 A1 | 9/2008 | Brewer |
| 2008/0262534 A1 | 10/2008 | O'Neil |
| 2008/0281351 A1 | 11/2008 | Croushorn et al. |
| 2008/0312682 A1 | 12/2008 | Shams et al. |
| 2009/0024159 A1 | 1/2009 | Nee et al. |
| 2009/0062842 A1 | 3/2009 | Esposito et al. |
| 2010/0049241 A1 | 2/2010 | Persson |
| 2010/0057120 A1 | 3/2010 | Kirkham |
| 2011/0178546 A1 | 7/2011 | Johnson et al. |
| 2011/0204114 A1 | 8/2011 | Miller |
| 2011/0214259 A1 | 9/2011 | Kosh et al. |
| 2011/0307004 A1 | 12/2011 | Johnson et al. |
| 2011/0313435 A1 | 12/2011 | Aldridge et al. |
| 2012/0071917 A1 | 3/2012 | McDonald et al. |
| 2012/0260463 A1 | 10/2012 | Hines |
| 2013/0012857 A1 | 1/2013 | Flynn et al. |
| 2013/0110019 A1 | 5/2013 | Hopman et al. |
| 2013/0110027 A1 | 5/2013 | Kobler |
| 2013/0145554 A1 | 6/2013 | Cane et al. |
| 2013/0296921 A1 | 11/2013 | Saunders et al. |
| 2013/0310872 A1 | 11/2013 | Croushorn et al. |
| 2014/0277103 A1 | 9/2014 | Esposito |
| 2015/0094756 A1 | 4/2015 | Kosiorek et al. |
| 2015/0133991 A1 | 5/2015 | Kosiorek et al. |
| 2016/0302799 A1 | 10/2016 | Esposito |
| 2018/0193033 A1 | 7/2018 | Kosiorek et al. |
| 2020/0022707 A1 | 1/2020 | Kosiorek et al. |
| 2020/0229826 A1 | 7/2020 | Kosiorek et al. |

FOREIGN PATENT DOCUMENTS

| | | |
|---|---|---|
| AU | 2014324593 B2 | 5/2018 |
| AU | 2018217338 A1 | 9/2018 |
| AU | 2014324593 C1 | 1/2019 |
| AU | 2018217338 B2 | 12/2020 |
| AU | 2018217338 B9 | 12/2020 |
| CA | 2929226 A1 | 4/2015 |
| CN | 201469344 U | 5/2010 |
| CN | 203169261 U | 9/2013 |
| DE | 2524968 A1 | 12/1976 |
| DE | 3047723 A1 | 7/1982 |
| DE | 3133793 A1 | 3/1983 |
| DE | 3232418 A1 | 3/1984 |
| EP | 0554602 A1 | 8/1993 |
| GB | 190721801 A | 12/1907 |
| GB | 191102140 A | 1/1912 |
| GB | 105170 A | 4/1917 |
| GB | 291600 A | 6/1928 |

(56) References Cited

FOREIGN PATENT DOCUMENTS

| | | |
|---|---|---|
| GB | 1206605 A | 9/1970 |
| GB | 2126649 A | 3/1984 |
| GB | 8324334 | 3/1984 |
| GB | 8324344 | 3/1984 |
| IN | 1702KOL2007 A | 6/2009 |
| WO | 9205741 A1 | 4/1992 |
| WO | 2005091718 A2 | 10/2005 |
| WO | 2011001431 A1 | 1/2011 |
| WO | 2011072126 A2 | 6/2011 |
| WO | 2012106683 A2 | 8/2012 |
| WO | 2015048660 A1 | 4/2015 |
| WO | 2015048668 A1 | 4/2015 |

OTHER PUBLICATIONS

"Combat Application Tourniquet, http://combattourniquet.com/about/, accessed Oct. 27, 2014.", Oct. 27, 2014.

"Communication Pursuant to Article 94(3) EPC Received for European Patent Office Application No. 14847757.3, Mailed on Apr. 22, 2020, 12 pages."

"Communication Pursuant to Article 94(3) EPC received for Application No. 14849448.7 mailed on Dec. 8, 2021, 4 pages".

"Communication Pursuant to Rules 161(2) and 162 EPC received for European Application No. 14847757.3, mailed on Feb. 2, 2017, 2 Pages."

"Communication pursuant to Rules 70(2) and 70a(2) EPC received for EP Application No. 14847757.3 on Jun. 12, 2018, p. 1".

"Corrected Notice of Allowability Received for U.S. Appl. No. 16/369,902, mailed on Mar. 8, 2022."

"Examiner's report Received for Canada Application 2,929,226, mailed on Aug. 13, 2021."

"Examiner's report Received for Canada Application 2,929,226, mailed on May 6, 2022."

"Examiner's report Received for Canada Application 2,929,226, mailed on Nov. 12, 2020."

"Examiner's report Received for Canada Application No. 2,929,223, mailed on Aug. 19, 2021."

"Examiner's report Received for Canada Application No. 2,929,223, mailed on Jun. 7, 2022."

"Examiner's report Received for Canada Application No. 2,929,223, mailed on Nov. 12, 2020."

"Extended European Search Report mailed for Application No. 14847757.3 on May 25, 2018".

"Extended European Search Report received for Application No. 14849448.7 mailed on Jun. 19, 2017, 9 pages".

"Final Office Action Received for U.S. Appl. No. 14/500,084, mailed on Mar. 31, 2017, 18 pages", 18.

"Final Rejection Received for U.S. Appl. No. 14/500,191 mailed on Sep. 12, 2017, 16 pages", 16.

"First Examination Report Received for AU Application No. 2018217338, mailed on Aug. 29, 2019, 6 pages".

"First Examination Report Received for AU Application No. 2020286253, mailed on Jan. 28, 2022, 3 pages".

"First Examination Report Received for Australian Application No. 2014324601, Mailed on Jun. 15, 2018, 4 Pages.", 4.

"International Preliminary Report on Patentability and Written Opinion received for PCT Application No. PCT/US2014/058079, Mailed on Mar. 29, 2016, 11 Pages."

"International Preliminary Report on Patentability and Written Opinion received for PCT Application No. PCT/US2014/058098, Mailed on Mar. 29, 2016, 9 Pages."

"International Search Report and Written Opinion received for PCT Application No. PCT/US2014/058079, mailed Jan. 22, 2015, 12 pages", Jan. 22, 2015, 12.

"International Search Report and Written Opinion Received for PCT Application No. PCT/US2014/058098, Mailed on Jan. 12, 2015, 10 Pages.", 10.

"Kragh Jr. et al., The military emergency tourniquet programs lessons learned with devices and designs. Military Medicine, 2011, vol. 176, No. 10. pp. 1144-1152.", pp. 1144-1152.

"Non-Final Office Action received for U.S. Appl. No. 14/500,084, mailed on Sep. 2, 2016, 18 pages", Sep. 2, 2016, 18.

"Non-Final Office Action Received for U.S. Appl. No. 15/847,033, mailed on Aug. 23, 2019, 52 pages".

"Non-Final Rejection Received for U.S. Appl. No. 14/500,191 mailed on Mar. 30, 2017, 21 pages", 21.

"Notice of Acceptance received for AU Application No. 2018217338, Mailed on Sep. 10, 2020."

"Notice of Acceptance Received for Australian Application No. 2014324601, Mailed on Apr. 15, 2019, 3 pages", May 2, 2019, 3.

"Notice of Allowance Received for U.S. Appl. No. 14/500,191, mailed on Dec. 31, 2018, 21 pages".

"Notice of Allowance Received for U.S. Appl. No. 14/500,191, mailed on Sep. 25, 2018, 10 pages".

"Notice of Allowance Received for U.S. Appl. No. 15/847,033 on Mar. 5, 2020 pp. 10."

"Notice of Allowance Received for U.S. Appl. No. 16/369,902, mailed on Dec. 8, 2021."

"Notice of Allowance Received for U.S. Appl. No. 16/790,536, mailed on Jul. 22, 2022."

"Notice of Allownace Received for U.S. Appl. No. 14/500,084 Mailed on Aug. 24, 2017, 7 pages", 7.

"Notice of Allownace Received for U.S. Appl. No. 14/500,084 Mailed on Jul. 31, 2017".

"Notice of Decision to Grant Received for Australian Patent Application No. 2014324601, Mailed on Aug. 15, 2019, 1 Page."

"Restriction Requirement Received for U.S. Appl. No. 16/369,902, mailed on Apr. 5, 2021."

"SAM Junctional Tourniquet, http:1/sammedical.com/wp-content/uploads/2013/09/SJT-206-BR0-4 web.pdf, accessed Oct. 28, 2014.", Oct. 28, 2014.

"Second Examination Report Received for AU Application No. 2018217338, mailed on Jul. 31, 2020".

"SOF Tactical Tourniquet Wide, http://www.tacmedsolutions.com/product/sof-tactical-tourniquet -wide/, accessed Oct. 27, 2014.", Oct. 27, 2014.

Walters, T.J. , et al., "Walters, T.J. , et al., "Laboratory Evaluation of Battlefield Tourniquets in Human Volunteers," USAISR Technical Report 2005-5, Sep. 30, 2005, 34 pages", Sep. 30, 2005, 34.

"Communication under Rule 71(3) received for EP Application No. 14847757.3 Mailed on Sep. 21, 2023."

"Notice of Allowance Received for Canada Patent Application No. 2,929,223, mailed on Aug. 3, 2023."

"Communication Pursuant to Article 94(3) EPC Received for European Patent Office Application No. 14847757.3, Mailed on Jun. 15, 2023."

MECHANICAL TOURNIQUET APPARATUS AND METHOD OF USE

CROSS-REFERENCE TO RELATED APPLICATIONS

This application is a continuation-in-part application that claims priority to:

U.S. patent application Ser. No. 16/369,902, filed Mar. 29, 2019 and now U.S. Pat. No. 11,324,516, which is a divisional application of U.S. patent application Ser. No. 14/500,191, filed Sep. 29, 2014 and now U.S. Pat. No. 10,271,855, which claims priority pursuant to 35 U.S.C. 119(e) to U.S. Provisional Patent Application Ser. No. 61/883,797, filed Sep. 27, 2013 (together, the "Pneumatic Tourniquet Applications"); and U.S. patent application Ser. No. 16/790,536, filed Feb. 13, 2020, which is a continuation-in-part application that claims priority:
  pursuant to 35 U.S.C. 119(e) to U.S. Provisional Patent Application Ser. No. 62/805,753, filed Feb. 14, 2018; and
  to U.S. patent application Ser. No. 15/847,033, filed Dec. 19, 2017 and now U.S. Pat. No. 10,716,577, which is a continuation application of U.S. patent application Ser. No. 14/500,084, filed Sep. 29, 2014 and now U.S. Pat. No. 9,855,055, which claims priority pursuant to 35 U.S.C. 119(e) to U.S.

Provisional Patent Application Ser. No. 61/883,769, filed Sep. 27, 2013 (together, the "Mechanical Tourniquet Applications"),
the entire disclosures of which are incorporated herein by reference.

GOVERNMENT RIGHTS

This invention was made with government support under W81XWH-12-P-0497 awarded by USA MED RESEARCH ACQ ACTIVITY. The government has certain rights in the invention.

FIELD

Embodiments of the present invention are directed to a tourniquet and novel blood flow restriction device. In more detail, embodiments of the present invention are directed to an emergency use, pre-fabricated tourniquet used for restricting flow of blood during extreme hemorrhage or exsanguination.

BACKGROUND

Exsanguination or major blood loss has been shown to be the major leading cause of death on the battlefield and directly correlates to major trauma in the civilian sector. Throughout history, tourniquets have been shown to save lives. Several large studies have confirmed the lifesaving benefit and low incidence of complications from pre-hospital use of tourniquets in combat casualties. Furthermore, the civilian Emergency Medical Services have adopted this opinion as well. Tourniquets are frequently used early in the care of trauma casualties because of the immediate lifesaving intervention capability and the speed with which they can be applied. Moreover, tourniquets are the standard of care for the temporary control of life-threatening extremity hemorrhage during the Care Under Fire (CUF) phase of the Tactical Combat Casualty Care (TCCC) in accordance with the Committee for Tactical Combat Casualty Care (CoTCCC) guidelines. These guidelines are becoming the standard of care for treatment of massive hemorrhage across the spectrum of pre-hospital care worldwide.

Due to the nature of traumatic amputation and dismemberment, there is a requirement for application of an emergency tourniquet to be operated by one hand. For a device to be truly operable by only one hand, it must be capable of being placed on an extremity, upper or lower, without having to perform fine motor skill functions. In general, tourniquet operation should not require the use of fine motor skills, regardless of the one-handed operability requirement, because tourniquets are generally only used during periods of extreme duress (i.e., when it is difficult or impossible to expect the use of fine motor skills).

Traditionally, tourniquets were nothing more than a general section of cloth material, usually a cravat, and a stick or dowel used as a windless. The general concept was to tighten the cloth material, reducing the circumference (diameter) of the cloth material against the extremity soft tissue, creating circumferential pressure sufficient enough to occlude blood flow. These make-shift tourniquets were often applied with too much pressure and caused neurovascular damage in limbs. Although the patient's life and limb were saved, the affected limb was permanently damaged. Therefore, a pre-fabricated tourniquet designed for consistent, even circumferential pressure is ideal for emergency use.

Additionally, current tourniquet designs are prone to failure and are generally ineffective for use on lower extremities. Pneumatic tourniquet designs can be desirable because pneumatic tourniquets can be more effective at restricting blood flow and can be more comfortable during use. However, because of design and cost constraints, current pneumatic tourniquets are generally only used in Hospital environments and are not effective or mechanically operable for field use.

There are many situations in which a tourniquet can save a life other than in military applications. Some recreational activities can be inherently dangerous and can cause severe injury requiring the use of such an emergency device, especially in a remote setting. Primary examples of this are camping, rock climbing, hiking, boating, etc. Footprint size and weight are always a consideration in such settings since the individual user is required to carry the device in a backpack. Therefore, a ruggedized pre-fabricated tourniquet made of the strong and light material would be best-suited for the end-user. Such a tourniquet would provide for efficient transportation and effective, life-saving utilization.

Thus, there is a need for a pre-fabricated tourniquet that is easy to apply, that ensures consistent and even circumferential pressure, that is light weight, that provides standard life saving operation, and that can be utilized in any setting or situation.

SUMMARY

One object of the general inventive concept is to provide a constricting tourniquet apparatus, such as a mechanical tourniquet and/or a pneumatic tourniquet.

A mechanical tourniquet apparatus of the present invention is made up of a tourniquet body, a carriage, a torsion bar, a receiver and a slider. The tourniquet body is long enough to encircle a human limb, for example, an arm or leg. The tourniquet body has two ends opposite one another. The tourniquet body has an interior side, intended to be positioned facing toward the limb. Opposite the interior side, the tourniquet body has an exterior side, intended to be positioned facing away from the limb.

Like the tourniquet body, the carriage also has an interior side and an exterior side, with the interior side intended to be positioned facing toward the limb and the exterior side intended to be positioned facing away from the limb. The carriage is attached to the tourniquet body between the two opposing ends of the tourniquet body so as to facilitate a generally uniform constriction pressure. The carriage also includes a torsion bar retainer that is configured to prevent or otherwise restrict movement of the torsion bar when the tourniquet is in a constricted configuration, thereby retaining the tourniquet in the constricted configuration.

The torsion bar retainer is part of a torsion bar retainer assembly that is moveable between an open configuration and a closed configuration. The retainer assembly includes a torsion bar retainer release for providing a mechanical advantage for moving the retainer assembly towards the open configuration. The retainer assembly further includes a stop that restricts movement of the retainer assembly, thereby preventing or otherwise reducing risk of damage to the retainer assembly.

A torsion bar is positioned on the exterior side of the tourniquet body and on the exterior side of the carriage. The torsion bar has two opposing ends and a middle portion. The middle portion has a slot sized and shaped such that a tightening strap can slide through the slot. Each of the two opposing ends are sized and shaped such that either can mate with the torsion bar retainer.

A tightening strap is positioned on the exterior side of the tourniquet body. The tightening strap has a middle portion and two opposite ends, at least the middle portion of the tightening strap being positioned on the exterior side of the carriage. The tightening strap is attached to the tourniquet body at each of the opposite ends of the tightening strap. The middle portion of the tightening strap passes through the slot of the torsion bar such that constriction of the tourniquet body is achievable by way of turning the torsion bar, thereby twisting the tightening strap. As the tourniquet body is constricted, a portion of the tourniquet body bunches up on the exterior side of the carriage.

A receiver is attached to one end of the tourniquet body. A slider is attached to the tourniquet body and positioned between the carriage and the end of the tourniquet body opposite the end with the receiver attached. The slider is sized and shaped to slide between various positions between the carriage and the end of the tourniquet body. The slider and receiver are sized and shaped to mate with one another. When the torsion bar is rotated, the tightening strap is tightened and the tourniquet body is pulled tighter. The tourniquet body is pulled equally in two opposite directions, toward the carriage.

Another object of the general inventive concept is to provide a method of making a mechanically constricting tourniquet apparatus. The method includes providing a tourniquet body, attaching a carriage, attaching a tightening strap, sliding a tightening strap through a slot in a torsion bar, attaching a receiver to one end of the tourniquet body, and attaching a slider to the tourniquet body.

The tourniquet body is long enough to wrap around a human limb, such as an arm or leg. The tourniquet body has two ends opposite each other. The tourniquet body also has an interior side intended to be positioned facing toward the limb. Opposite the interior side, the tourniquet body has an exterior side, intended to be positioned facing away from the limb.

Like the tourniquet body, the carriage also has an interior side intended to be facing toward the limb and an exterior side opposite the interior side intended to be facing away from the limb. The carriage also includes a torsion bar retainer. The carriage is attached to the tourniquet body such that the carriage remains positioned between the two opposing ends of the tourniquet body.

The tightening strap has a middle portion and two opposite ends. The tightening strap is attached to the tourniquet body at each of the opposite ends of the tightening strap and with the carriage positioned between the opposite ends of the tightening strap. The tightening strap is positioned on the exterior side of the tourniquet body and on the exterior side of the carriage.

The torsion bar has two opposing ends and a middle portion. The torsion bar is positioned on the exterior side of the tourniquet body and on the exterior side of the carriage. The middle portion of the torsion bar includes a slot sized and shaped such that the tightening strap can slide through the slot. The tightening strap is slid through this slot. Each of the two opposing ends of the torsion bar are sized and shaped to mate with the torsion bar retainer of the carriage. When the torsion bar is rotated, the tightening strap is tightened and the tourniquet body is pulled tighter. The tourniquet body is pulled equally in two opposite directions, toward the carriage.

A receiver is attached to one end of the tourniquet body. A slider is attached to the tourniquet body between the carriage and the other end of the tourniquet body. The slider can be slid to a plurality of different positions between the carriage and the end of the tourniquet body opposite the receiver. The slider and receiver are sized and shaped to mate with one another.

A pneumatic tourniquet apparatus of the present invention is made up of a bladder, a reservoir chassis, a retaining cover, a receiver and a slider. The bladder is elongated in shaped—long enough to wrap around most human limbs. In some embodiments, the bladder is formed from a single sheet of plastic, folded over along one edge and sealed along the other three edges so that the bladder holds and maintains air pressure while being inflated.

The reservoir chassis holds and protects the bladder. The reservoir chassis includes a main section that envelops the bladder and a reservoir chassis extension section that extends from the main section but does not envelop the bladder. A retaining cover attached to the reservoir chassis where the main section and the chassis extension section connect. The retaining cover covers and protects the reservoir chassis.

A receiver is connected to either the reservoir chassis or the retaining cover, at a location very near to where the retaining cover is attached to the reservoir chassis. A slider is connected to the retaining cover such that the slider can be slid to any point along the retaining cover. The receiver and slider are sized and shaped such that the slider is temporarily locked in position on the retaining cover as a friction buckle when engaged with the receiver.

Another object of the general inventive concept is to provide a pneumatically constricting tourniquet apparatus. The pneumatic tourniquet apparatus is made up of a bladder placed into a reservoir chassis, a retaining cover attached to the reservoir chassis, a receiver attached to the retaining cover or the reservoir chassis, and a slider attached to the retaining cover. The reservoir chassis includes a main section that holds the bladder and an extension section connected to the main section. The retaining cover is attached to the reservoir chassis at a position adjacent to where the main section of the reservoir chassis connects to the extension section. The receiver is attached to either the retaining cover or the reservoir chassis adjacent to the position where the retaining cover is attached to the reservoir chassis. The slider is attached to the retaining cover such that the slider can slide to numerous positions along the retaining cover. The slider is sized and shaped to engage with the receiver.

Another object of the general inventive concept is to provide a method of making a pneumatically constricting tourniquet apparatus. The method includes sealing a bladder, inserting the bladder into a reservoir chassis, attaching a retaining cover to the reservoir chassis, connecting a receiver to either the reservoir chassis or the retaining cover, and connecting a slider to the retaining cover. In some embodiments, the bladder is formed from a single sheet of plastic, folded over along one edge and sealed along the other three edges so that the bladder holds and maintains air pressure while being inflated. The bladder is inserted into the reservoir chassis to hold and to protect the bladder. The reservoir chassis includes a main section that envelops the bladder and a reservoir chassis extension section that extends from the main section but does not envelop the bladder. The retaining cover is attached to the reservoir chassis where the main section and the chassis extension section connect. The retaining cover covers and protects the reservoir chassis.

A receiver is connected to either the reservoir chassis or the retaining cover at a location near where the retaining cover is attached to the reservoir chassis. The slider is connected to the retaining cover such that the slider can be slid to any point along the retaining cover. The receiver and slider are sized and shaped such that the slider is temporarily locked in position on the retaining cover as a friction buckle when engaged with the receiver.

Another object of the general inventive concept is to provide a method of making a pneumatically constricting tourniquet apparatus. The method includes placing a bladder into a reservoir chassis, attaching a retaining cover to the reservoir chassis, attaching a receiver to the retaining cover or the reservoir chassis, and attaching a slider to the retaining cover. The reservoir chassis includes a main section that holds the bladder and an extension section connected to the main section. The retaining cover is attached to the reservoir chassis at a position adjacent to where the main section of the reservoir chassis connects to the extension section. The receiver is attached to either the retaining cover or the reservoir chassis adjacent to the position where the retaining cover is attached to the reservoir chassis. The slider is attached to the retaining cover such that it can be slid along the retaining cover. The slider is sized and shaped to engage with the receiver.

The foregoing and other objects are intended to be illustrative of the invention and are not meant in a limiting sense. Many possible embodiments of the invention may be made and will be readily evident upon a study of the following specification and accompanying drawings comprising a part thereof. For example, dimensional values included herein are provided for exemplary purposes, and embodiments of the present invention contemplate tourniquets or tourniquet components having a various dimensional values. Furthermore, various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

BRIEF DESCRIPTION

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
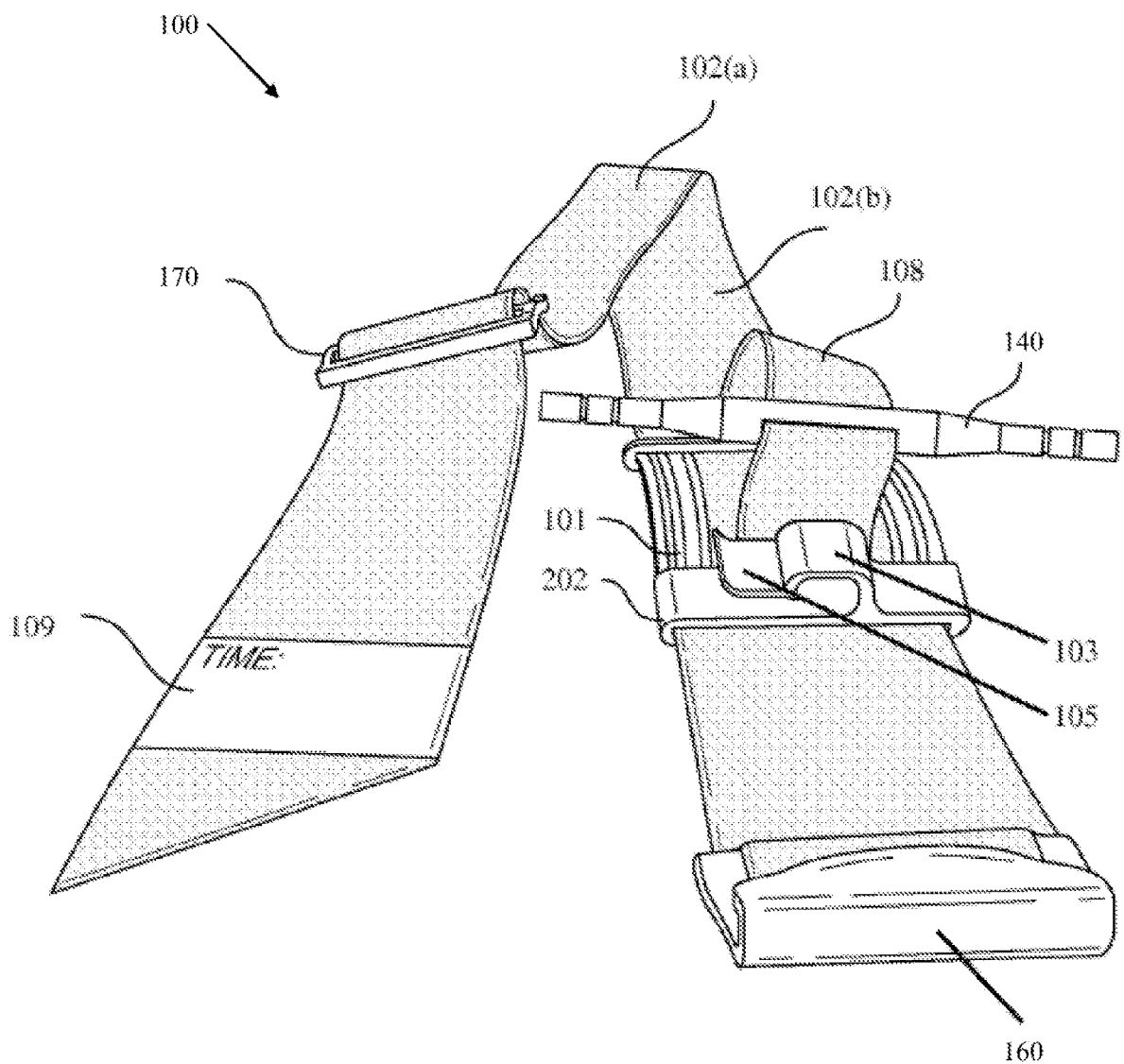
FIG. 1 shows an exemplary mechanical tourniquet according to an embodiment of the general inventive concept.
Figure 6:
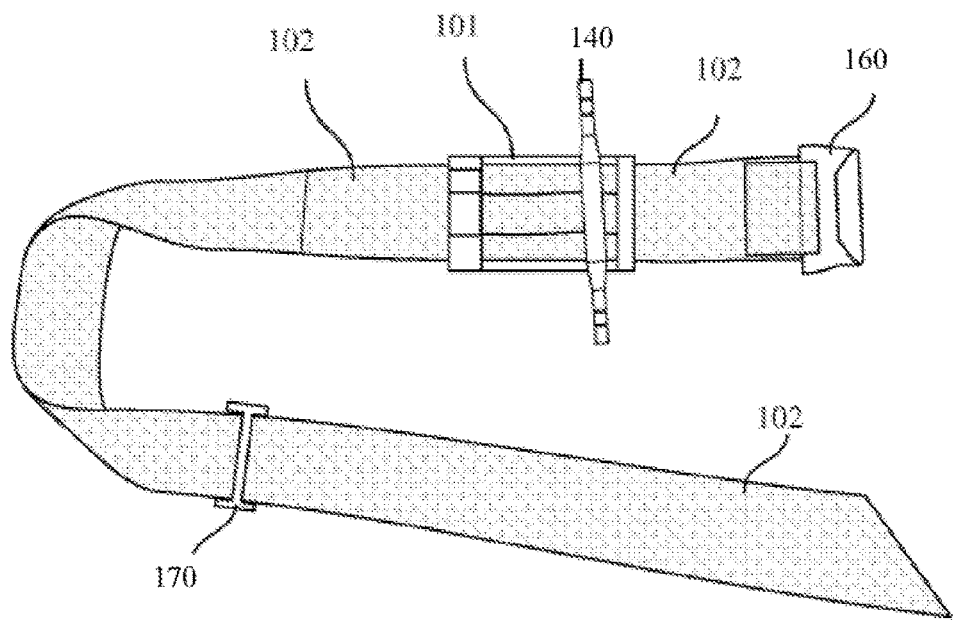
FIG. 6 shows an additional view of the tourniquet from FIG. 1.
Figure 7:
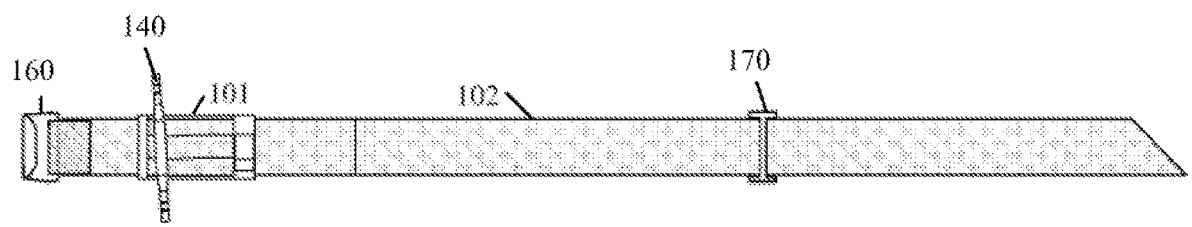
FIG. 7 shows still another view of the tourniquet from FIG. 1.
Figure 8:
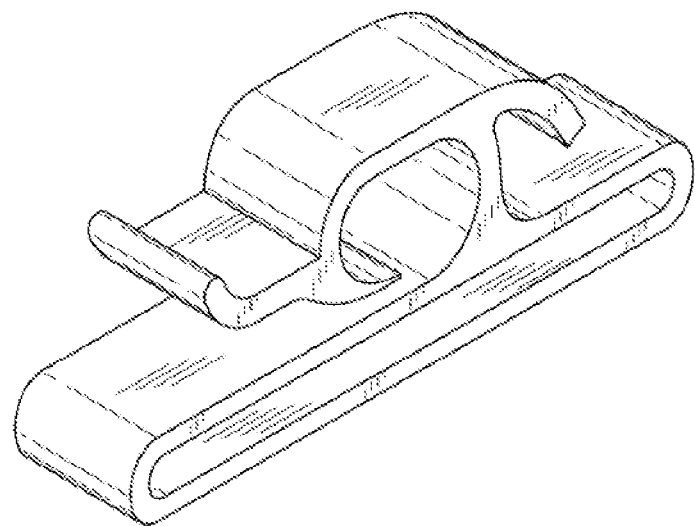
FIG. 8 is a perspective view of a retainer assembly of an embodiment of the present invention.

With reference to FIG. 1, embodiments of the present invention include a mechanical tourniquet 100 for restricting a flow of blood in a body part, such as an upper or a lower extremity. In certain embodiments, the mechanical tourniquet 100 is comprised of: (a) a carriage 101 (See also FIG. 2) at a central point of a tourniquet body 102, with the carriage 101 acting as an attachment point and as a base plate for mechanical action, and including a torsion bar retainer 103 that holds a torsion bar 140 (See also FIG. 3) in place once tension is created by a twisting action (i.e., twisting or turning the torsion bar), with the torsion bar retainer 103 being releasable upon demand by lifting on a torsion bar retainer release 105; (b) the torsion bar 140 connected to the tourniquet body 102 and acting as a fulcrum to twist a tightening strap 108 so as to shorten a length of a diameter of the tourniquet body 102; (c) a receiver 160 (See also FIG. 4) for accepting a slider 170 (See also FIG. 5) on the tourniquet body 102 from any position along the tourniquet body 102 on a long free running side short of the carriage 101 itself, with the receiver 160 allowing a user to "snap" the slider 170 into place, and furthermore, the receiver 160 is attached to the short end of tourniquet body 102 that runs through the carriage 101; (d) the slider 170 operates as a friction buckle and is positioned along any section of the tourniquet body 102 by being attached to the long free running end of the tourniquet body 102, and furthermore, the slider 170 includes a round side bar and a square side bar with grippers for allowing free rotation when attached to the receiver 160; and (e) the tourniquet body 102 (See also FIGS. 6-7) operating in conjunction with the above-described components (i.e., components a-d). In operation, the tourniquet is operable to create a continuous loop that is placed around an extremity to accomplish circumferential pressure to restrict blood flow. A rotation of the torsion bar 140 through the tightening strap slot shortens the diameter of the continuous loop creating a radial compression force against the extremity.

With respect to the embodiment shown in FIG. 1, the back face of the tourniquet body 102 is shown as 102(*a*). The back face 102(*a*) of the tourniquet body 102 is the interior side and is intended to be positioned such that it is facing toward the limb/extremity. In some embodiments, the tourniquet body 102 is comprised of nylon material. The front face of the tourniquet body 102 is shown as 102(*b*). The front face 102(*b*) of the tourniquet body 102 is the exterior side and is intended to be positioned such that it is facing away from the limb/extremity. In some embodiments, the front face 102(*b*) of the tourniquet body 102 includes dual hook and loop fasteners such that the tourniquet body 102 can be attached to itself.

Still referring to FIG. 1, the tightening strap 108 is a strip of material smaller in size than the tourniquet body 102. The tightening strap 108 is connected to the tourniquet body 102 on both sides of the carriage 101. The tightening strap 108 is routed through a slot in the torsion bar 140. The tightening strap 108 provides a constricting action by pulling both sides of the tourniquet body 102 when the torsion bar 140 is twisted.

In some embodiments, the tourniquet body 102 further includes a blank label 109. The blank label 109 may be used to write the time when the tourniquet is applied or various other relevant notes regarding patient care.

In some embodiments, the carriage 101 includes a strap holder to hold the tourniquet body 102 stable when operating the tourniquet.

In more detail, and with reference to FIGS. 1, 2, and 6-7, the carriage 101 will act as the base for the action of twisting the torsion bar 140. In some embodiments, the carriage 101 has both a niche 201 and a narrow 210 bridge at either end of the carriage base itself, for allowing the tourniquet body 102 strap material to move efficiently through and in line when turning the torsion bar 140. The carriage 101 is ruggedized for durability but has, in some embodiments, a flex and gradual curve that provides the carriage 101 with the ability to conform to both small and large limbs. As such, the carriage 101 allows for application on both upper and lower extremities regardless of size or composition of the extremities to which the tourniquet is being applied. In some embodiments, the tourniquet will be capable of being applied to adult human beings with extremities that are sized between the $5^{th}$ to $95^{th}$ percentile.

Figure 2:
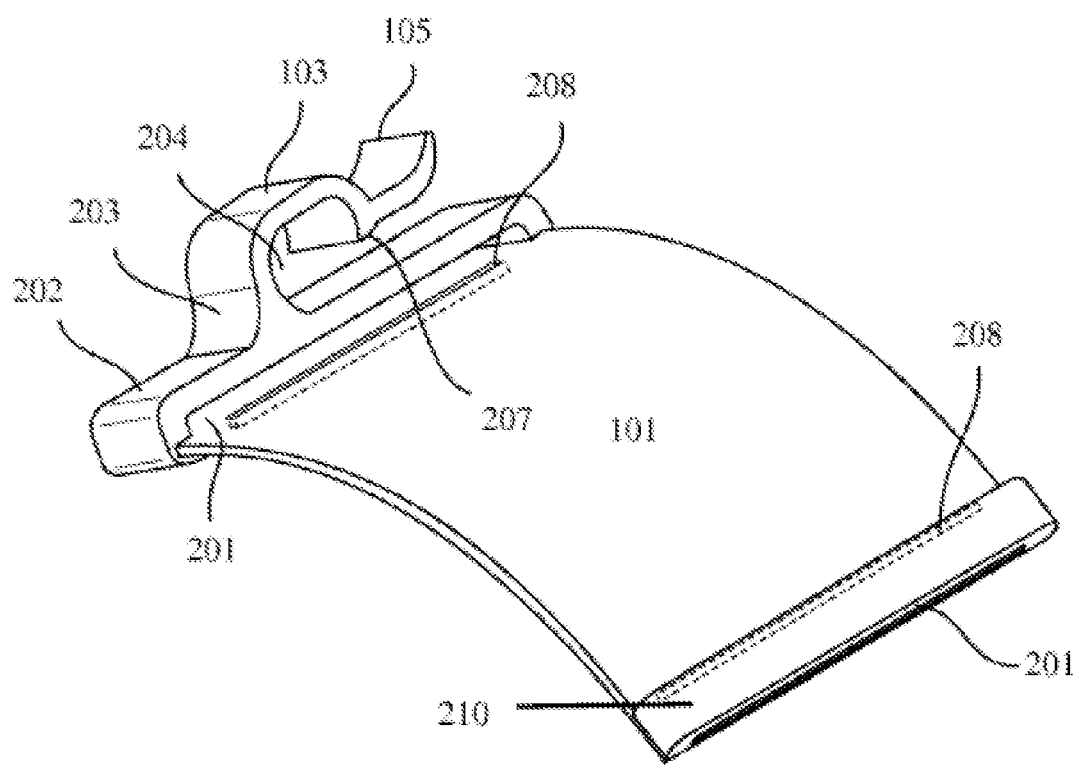
FIG. 2 shows an exemplary carriage of the tourniquet from FIG. 1.

Referring to FIG. 2, the carriage 101 includes a niche 201 at either end of the carriage 101. The niche 201 is sized and shaped to allow the tourniquet body 102 to move easily through the niche 201 when the torsion bar 140 is twisted. In some embodiments, a niche 201 is included on both ends of the carriage 101. The niche 201 allows the tourniquet body 102 to pass through the bridges (202 and 210) and helps to squeeze the tourniquet. In some embodiments, the carriage includes a wide bridge 202 and a narrow bridge 210. The narrow bridge 210 allows for easy travel of the tourniquet body 102 through the carriage 101 as the tourniquet is tightened. The wide bridge 202 holds the torsion bar retainer 103 and provides space for a niche 201. The wide bridge 202 and niche 201 provide a "tunnel" passage for the tourniquet body 102 to pass through as the tourniquet is tightened. A torsion bar retainer supporter 203 connects the torsion bar retainer 103 to the wide bridge 202. The torsion bar retainer supporter 203 prevents diffraction of the retainer 103 when the torsion bar 140 is released.

Still referring to FIG. 2, when the torsion bar 140 is twisted and the tourniquet body 102 is drawn in, an end of the torsion bar 140 is placed into the torsion bar retainer 103 and is held secure in a torsion bar receptacle 204. An end of the torsion bar 140 is placed into the torsion bar receptacle 204 after the torsion bar 140 is twisted. The torsion bar 140 is held in place by the torsion bar retainer 103 so that circumferential pressure remains stable. In some embodiments, the torsion bar retainer 103 includes a spur 207 to better secure the torsion bar 140 in place in the retainer 103. The torsion bar retainer release 105 provides a mechanism of mechanical movement to release the torsion bar 140 from the retainer 103. In some embodiments, the retainer includes a stop (205, FIG. 9) for limiting such mechanical movement.

Still referring to FIG. 2, in some embodiments, the carriage 101 includes one or more holder slots 208. The holder slots 208 are spaces for carriage holders to hold the carriage in place. In some embodiments, the carriage 101 includes a base plate for the torsion bar 140 and torsion bar retainer 103. As the torsion bar 140 is twisted, the base plate provides structure to absorb and disperse forces circumferentially. The base plate assists in application and tightening of the torsion bar 140. In some embodiments, the base plate has a slight curvature. In some embodiments, the base plate has an approximately 33 degree inclination.

In additional embodiments, and with reference to FIGS. 1-3, and 6-7, the torsion bar retainer 103 of the carriage 101 is operable for retaining either end of the torsion bar 140 once circumferential pressure is applied (i.e., by turning/twisting the torsion bar 140). The torsion bar 140 is held in place by a spur 207 affixed to the tip of the retainer 103. Furthermore, the torsion bar retainer 103 includes a torsion bar retainer release 105, which provides better movement and application for releasing the retained torsion bar 140 while under pressure. The torsion bar retainer 103 is integrally formed with the carriage 101 by the torsion bar retainer supporter 203 which prevents breakage and diffraction when retaining or releasing the torsion bar.

Figure 9:
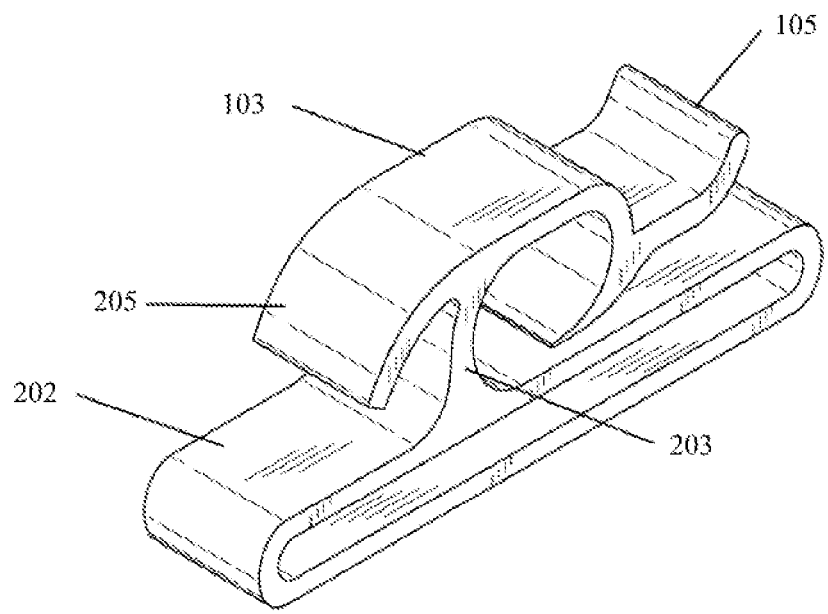
FIG. 9 is a perspective view of the retainer assembly of FIG. 8, shown from a different angle.
Figure 10:
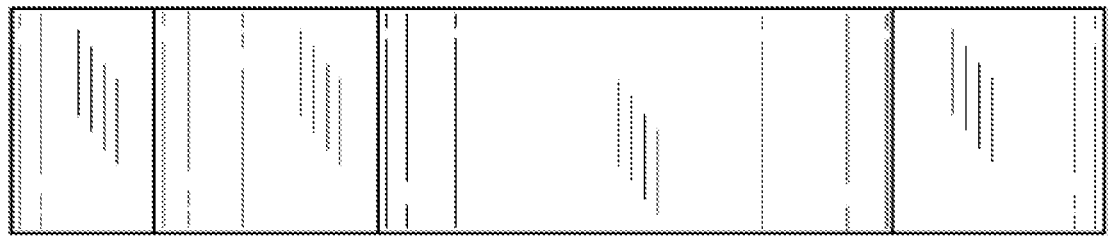
FIG. 10 is a top plan view of the retainer assembly of FIG. 8.
Figure 11:
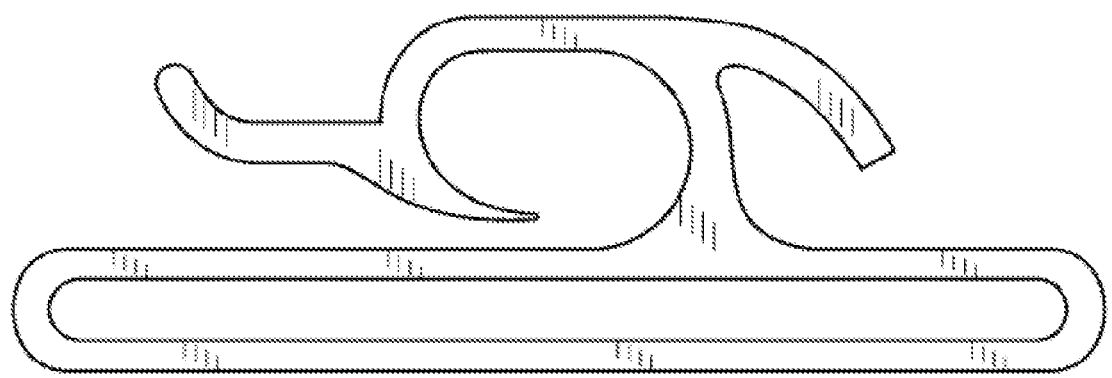
FIG. 11 is a front elevation view of the retainer assembly of FIG. 8.
Figure 12:
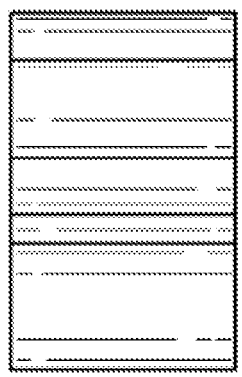
FIG. 12 is a first side elevation view of the retainer assembly of FIG. 8.
Figure 13:
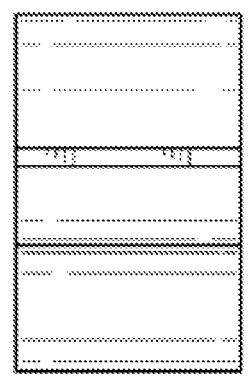
FIG. 13 is a second side elevation view of the retainer assembly of FIG. 8.

Referring to FIG. 2 and FIG. 9, some embodiments of the present invention include a retainer assembly defining a receptacle 204 or other space for receiving an end of a torsion bar 140, thereby preventing or otherwise inhibiting rotation of the torsion bar 140. The retainer assembly is moveable between a closed configuration and an open configuration. In the open configuration, the retainer assembly is configured to allow the torsion bar to move in and out of the receptacle 204. In the closed configuration, the retainer assembly is configured to prevent or otherwise inhibit the torsion bar from moving into or out of the receptacle 204, as applicable.

In some embodiments, the retainer assembly includes a torsion bar retainer 103 that is hingedly coupled to a base member, such as the carriage 101, a bridge 202, or the like. In some embodiments, a torsion bar retainer support 203 extends between the base and the torsion bar retainer 103, thereby facilitating rotation of the torsion bar retainer 103 relative to the base. In some embodiments, the torsion bar retainer 103 is rotatable between a first position and a second position relative to the base, the first and second positions of the torsion bar retainer 103 being associated with the closed and open configurations of the retainer assembly, respectively. In some embodiments, the retainer assembly includes a stop 205 for preventing the torsion bar retainer 103 from moving beyond a third location relative to the base. In this way, the stop 205 reduces risk of damage to the retainer assembly, such as by reducing bending of the torsion bar retainer support 203. It will be appreciated that a first distance between the first and second positions of the torsion bar retainer 103 is less than or equal to a second distance between the second and third positions of the torsion bar retainer 103.

In some embodiments, the stop 205 extends from a distal end of the torsion bar retainer support 203 and/or from a proximal end of the torsion bar retainer 103. In some embodiments, the stop 205 extends towards the base such that a distal end of the stop 205 engages with the base when the torsion bar retainer 103 is in the third position, the distal end of the stop 205 being displaced from the base when the torsion bar retainer 103 is in the first position.

Figure 3:
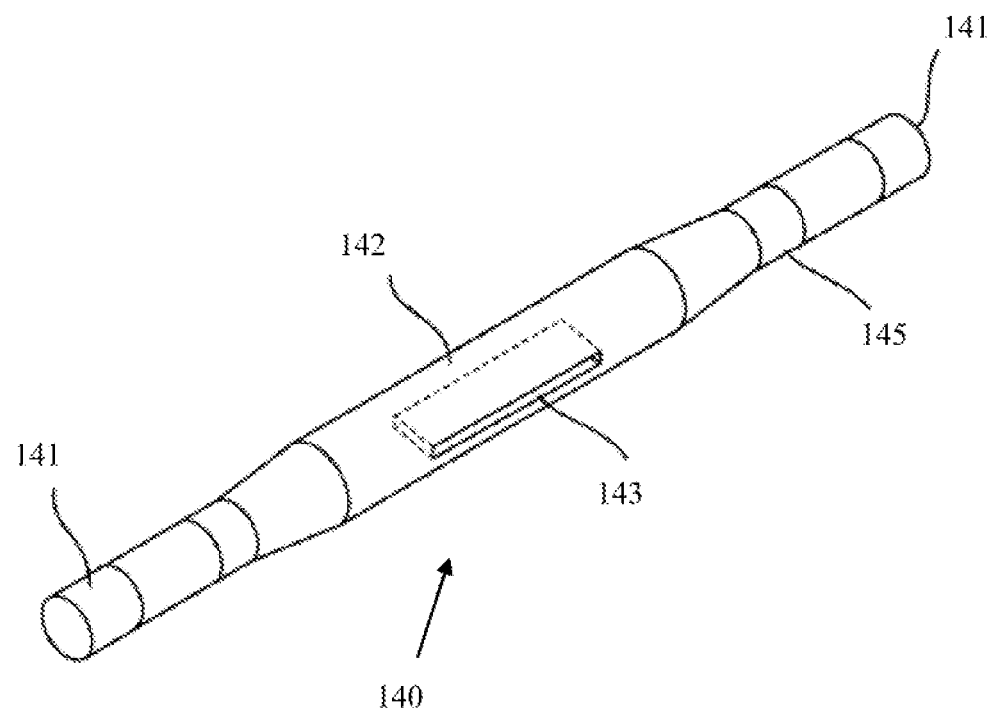
FIG. 3 shows an exemplary torsion bar of the tourniquet from FIG. 1.

Referring to FIG. 3, the torsion bar 140 of an embodiment is shown. The torsion bar 140 includes an end portion 141 at both ends. The end portion 141 is the part of the torsion bar 140 that is placed into the torsion bar receptacle (204 of FIG. 2) to hold the torsion bar 140 in place. The torsion bar 140 also includes a middle portion 142 that is thicker than the end portion 141. The middle portion 142 supports the tightening strap slot 143. The middle portion 142 is sized and shaped to reduce the chance of failure of the torsion bar 140 during application and tightening of the tourniquet. The tightening strap slot 143 is a slot in the middle portion 142 of the torsion bar 140 through which the tightening strap (108 of FIG. 1) is routed. In some embodiments, the torsion bar 140 is circular in cross section with a preferred diameter of approximately 0.3 inches. In some embodiments, the torsion bar 140 includes torsion bar grips 145, which are checker-board-style grooves to improve friction, grip, and tactile sensitivity when applying the tourniquet.

Furthermore, with reference to FIGS. 1-2, and 6-7, the carriage plate of the carriage 101 has holder slots 208 to secure the carriage 101 to the tourniquet body 102 and to hold the carriage 101 in place during use of the tourniquet.

With reference to FIG. 1, additional embodiments of the present invention include a tourniquet for restricting a flow of blood in a body part, such as an upper or a lower extremity, with the tourniquet comprising: (a) a short end (See also FIGS. 6-7) of a tourniquet body 102 attached to a carriage 101 (See also FIG. 2); (b) a long running end of the tourniquet body 102 attached to the carriage 101, furthermore a receiver 160 (See also FIG. 4) and a slider 170 (See also FIG. 5) are capable of being secured together so as to anchor the long running end of the tourniquet body 102 to the short end of the tourniquet body 102 near where the carriage 101 is attached to the tourniquet body 102, furthermore still, the slider 170 allows for positional adjustment anywhere along the long running end of the tourniquet body 102 short of the carriage attachment point itself; (c) the tourniquet body 102 connects with the carriage 101 at an attachment point of the tourniquet body 102, with the connection being achieved by two holder slots 208 of the carriage, with such holder slots 208 being integrally formed with the carriage 101 (such as by a continuous mold), and as such, the tourniquet body 102 extends through the carriage 101 in a generally continuous manner, furthermore still, the tourniquet body 102 does not contain any breaks throughout its entire length, thus creating a continuous loop of tourniquet body 102, and furthermore still, the only attachment point of the continuous, tourniquet body 102 loop is where the tourniquet body 102 is attached to the receiver 160; (d) a tightening strap 108 (See also FIGS. 6-7) attached to the short end and long free running end of the tourniquet body 102, with the tightening strap 108 running through a middle portion 142 of a torsion bar 140 (See also FIG. 3), and with the tightening strap 108 functioning as a shortening action mechanism of the tourniquet body 102, when twisted by way of the torsion bar 140; (e) the mechanical shortening action is performed by pulling together (i.e., a shortening) the short and free running long end of the tourniquet body 102 over the carriage 101, through the niche 201 and narrow bridge 210, by way of the tightening strap 108, so as to create a circumferential pressure of the continuous tourniquet body 102 loop around an extremity.

In certain embodiments, the tourniquet includes a torsion bar 140 (See FIG. 3) that is approximately 0.3 inches in diameter and comprised of one middle 142 and two end portions 141. The diameter of the torsion bar 140 allows for ease and non-restrictive placement and allows for simple release of the torsion bar retainer 103. A middle portion 142 of the torsion bar 140 includes a tightening strap slot 143 where the tightening strap 108 is secured in place ensuring tourniquet body shortening action when the torsion bar 140 is twisted and pressure is applied. Furthermore, the torsion bar 140 includes torsion bar grips 145 that are grooved into the end portions 141 of the torsion bar 140 to increase tactile sensitivity. The middle portion 142 of the torsion bar 140 also has a textured rough surface to decrease the possibility of slippage when applying pressure during the mechanism of action.

Figure 4:
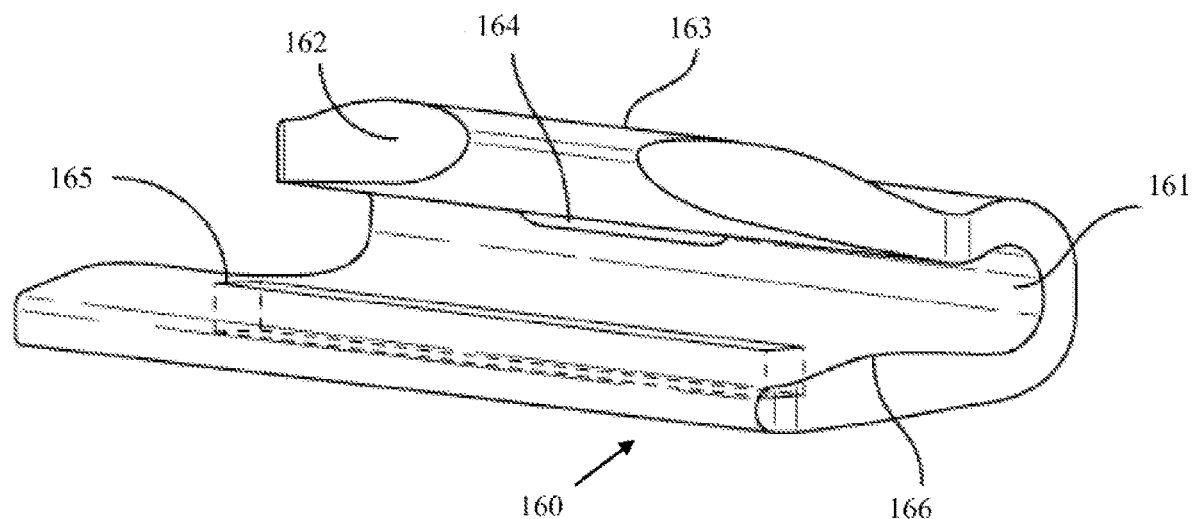
FIG. 4 shows an exemplary receiver of the tourniquet from FIG. 1.

As illustrated in FIG. 4, the receiver 160 includes a hook-shaped catch 161 that the round side bar 171 of the slider 170 (See FIG. 5) can be place into or removed from by the user on demand through application of the receiver flange 162. A lip portion 163 of the receiver 160 is the narrower portion of the receiver 160 and facilitates ease of placement for the round side bar 171 of the slider 170, and the bar locks the hook slider into place.

With respect to FIG. 4, in some embodiments, the hook-shaped catch 161 (or slider niche) is sized and shaped to mate with and receive the slider 170 and lock the slider 170 securely in place. The receiver flange 162 guides and provides an easy placement for the slider 170 which locks the tourniquet body in place. The flange 162 slopes upward to facility placement. The lip 163 is a narrower part of the receiver 160 to provide an easy placement with the receiver flange 162 for the slider 170. A bar 164 hangs down from the lip 163. The bar 164 supports locking of the hook slide and prevents unintentional displacement (dislodging) of the slider 170 from the receiver 160. The bar 164 allows the slider 170 to "snap" or audibly "click" when the slider 170 and receiver 160 are properly mated. A supporter 166 is a thicker portion of the receiver 160 that structurally supports the receiver slot 165. The receiver slot 165 is a space for a receiver holder to connect the receiver 160 to the tourniquet body 102.

Figure 5:
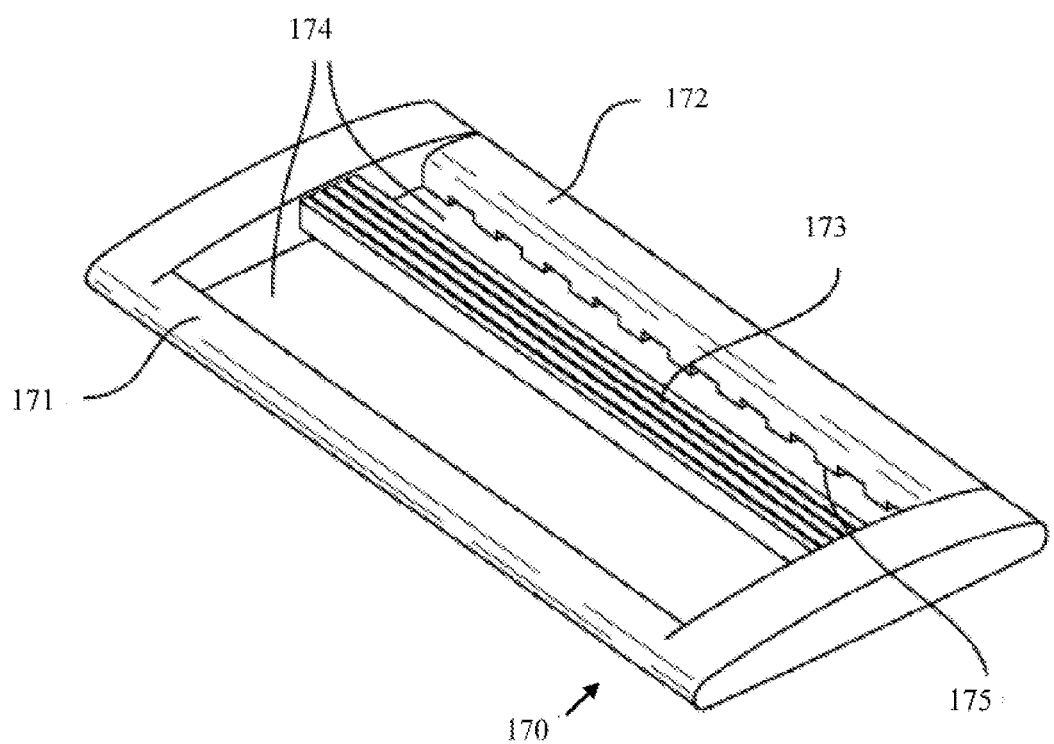
FIG. 5 shows an exemplary slider of the tourniquet from FIG. 1.

With reference to FIG. 5, the slider 170 functions as a friction buckle that is operable to be placed anywhere on the tourniquet long body 102 free running end of the tourniquet, short of the carriage attachment hook. The square side bar 172 of the slider 170 with protruding grippers 505 facilitates friction when the round side bar 171 is placed into the receiver 160 (See FIG. 4), thus stopping slippage, yet allowing excess slack to be removed from the diameter of the circumferential tourniquet body 102 upon demand from the user with an upward pulling motion of the tourniquet long body. Furthermore, the tourniquet long body 102 can be pre-routed through the slider 170, thus avoiding the necessity to route the long free running end of the tourniquet body 102 through the slider 170 during use.

With respect to FIG. 5, in some embodiments, the slider 170 includes a round edge 171 (or round side bar). The round side bar 171 is sized and shaped to interface with the receiver 160. The round side bar 171 is sized and shaped to allow for articulation when mated with the receiver 160. The slider 170 further includes a frame 172 (or square side bar). The square side bar 172 gives support, structure and shape to the slider 170. In some embodiments, the slider 170 will be a distinctive color to easily and quickly visually distinguish the slider's position relative to the tourniquet body 102. For example, in some embodiments, the slider 170 is coyote brown. In some embodiments, the slider 170 includes a slider friction bar 173. The slider friction bar 173 provides friction and inhibits the release of tension when the tourniquet is applied. The friction bar 173 is positioned higher than the side bars 171 and 172. The friction bar 173 is sized and shaped to lock the slider 170 in position when the tourniquet is applied. The slider 170 further includes slider gaps 174. The tourniquet body 102 is routed through the slider gaps 174 with dual hook and loop fasteners on the tourniquet body 102 side that faces toward the slider friction bar 173. The square side bar 172 of the slider 170 also includes grippers 505. The grippers 505 facilitate friction when the round slider bar 171 is placed into the receiver 160. This stops slippage, yet allows excess slack to be removed from the tourniquet body 102 continuous loop upon demand with an upward pulling motion of the tourniquet body 102 long running end.

Together, the slider 170 (See FIG. 5) and the receiver 160 (See FIG. 4) function as a buckle to attach the tourniquet long body free running end and the tourniquet short body end of the tourniquet, so as to create a continuous loop. Adjustments can be made, via the slider 170, for shortening or lengthening the continuous loop once applied, and/or the slider 170 can be attached or detached from the receiver 160 to facilitate ease of application by the user.

With reference to FIG. 1, further embodiments of the present invention include tourniquet designed for restricting a flow of blood in a body part, such as an upper or a lower extremity, with the tourniquet comprising: (a) a tourniquet body 102 (See also FIGS. 6-7) that is approximately 2 inches wide by approximately 39 inches long, after attachment of the receiver 160 (See also FIG. 4) and the carriage 101 (See also FIG. 2), with such a length including a length of the receiver 160 itself; (b) the tourniquet body 102 includes a front face of a material having dual hook and loop, which allows an excess portion of the long free running end to attach back onto itself once applied, furthermore, the dual hook and loop assists in securing the long free running end of the tourniquet body 102 on the free running side of the slider (See also FIG. 5) creating additional friction and a locking mechanism, furthermore still, a slider friction bar 173 of the slider 170 and the dual hook and loop serve as a two piece locking mechanism when applied as described herein; (c) a tightening strap 108 (See also FIGS. 6-7) is routed through a torsion bar slot 143 of a torsion bar 140 (See also FIG. 3) and connects the short end and long free running end of the continuous loop. The tightening strap 108 is the mechanism of action, such that twisting the torsion bar 140 provides constriction by pulling both sides of the tourniquet body 102 during the application of the tourniquet.

The width of the tourniquet (See FIGS. 1 and 6-7) increases circumferential compression of the soft tissue on the extremity, thus promoting effective occlusion of vessels and achieving better restriction of blood flow, while reducing the amount of circumferential pressure required within the band of the tourniquet. In some embodiments, the 2 inch width of the tourniquet provides an optimal width for functionality, efficacy, weight and cube. The tourniquet body 102 may, in some embodiments, be made from various types of elastic and/or inelastic flexible material, such as woven fabric, vinyl, leather, neoprene, nylon, etc. Furthermore, other components of the tourniquet (e.g., carriage 101, receiver 160, slider 170, torsion bar 140) may be made from rigid or semi-rigid materials, such as various types plastics, metals, or the like.

Furthermore, the slider 170 (See FIG. 5) and the receiver 160 (See FIG. 4) combine to function as a buckle device that can be easily attached and detached to facilitate application on upper or lower extremities. When seated in the receiver 160, the round side bar 171 of the slider 170 pivots, allowing for ease of tightening the free long running end of tourniquet body 102 through the slider 170 and allowing for rapid sizing of the tourniquet on an upper or a lower extremity.

Figure 14:
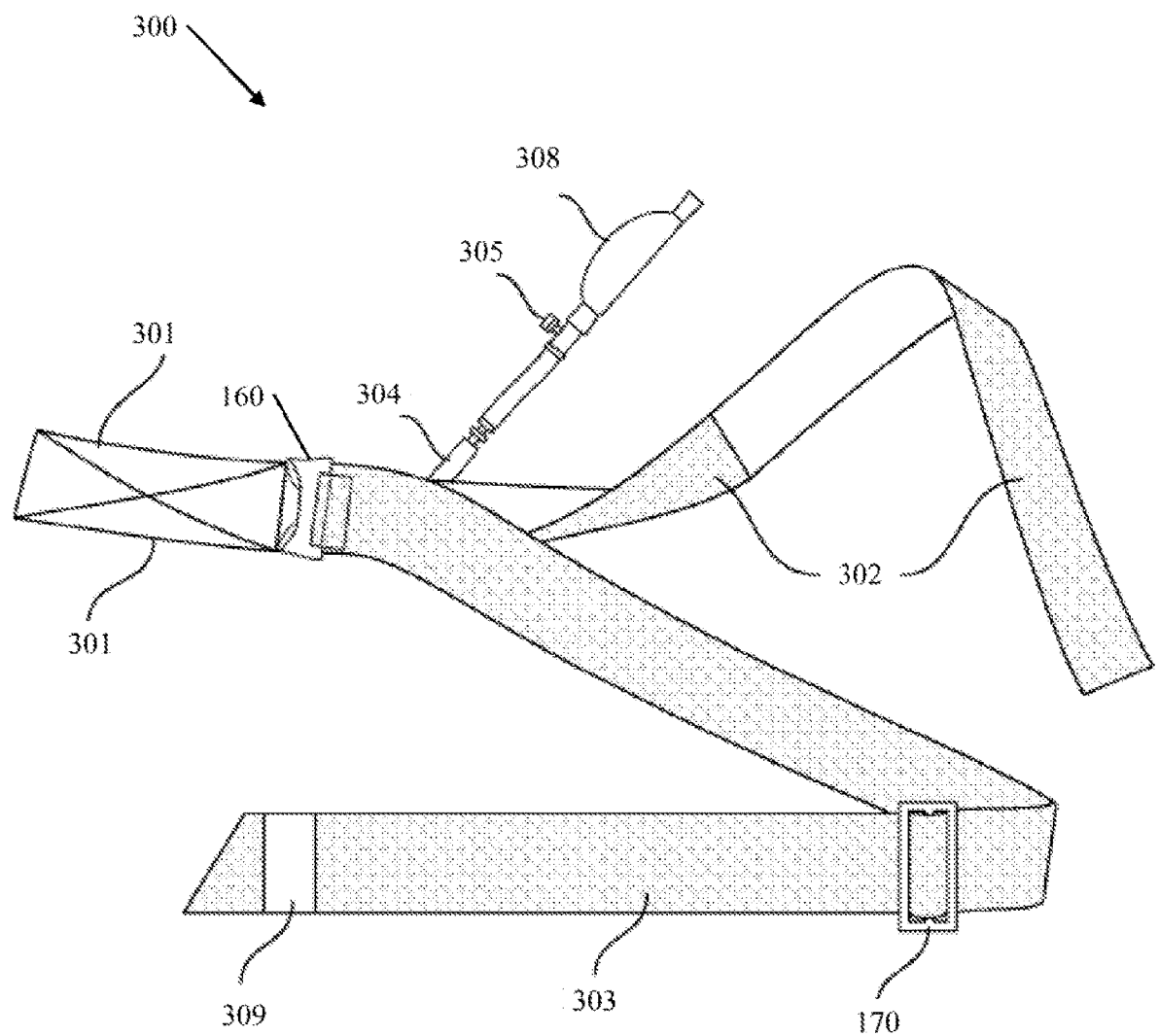
FIG. 14 shows an exemplary pneumatic tourniquet according to embodiments of the present invention.
Figure 15:
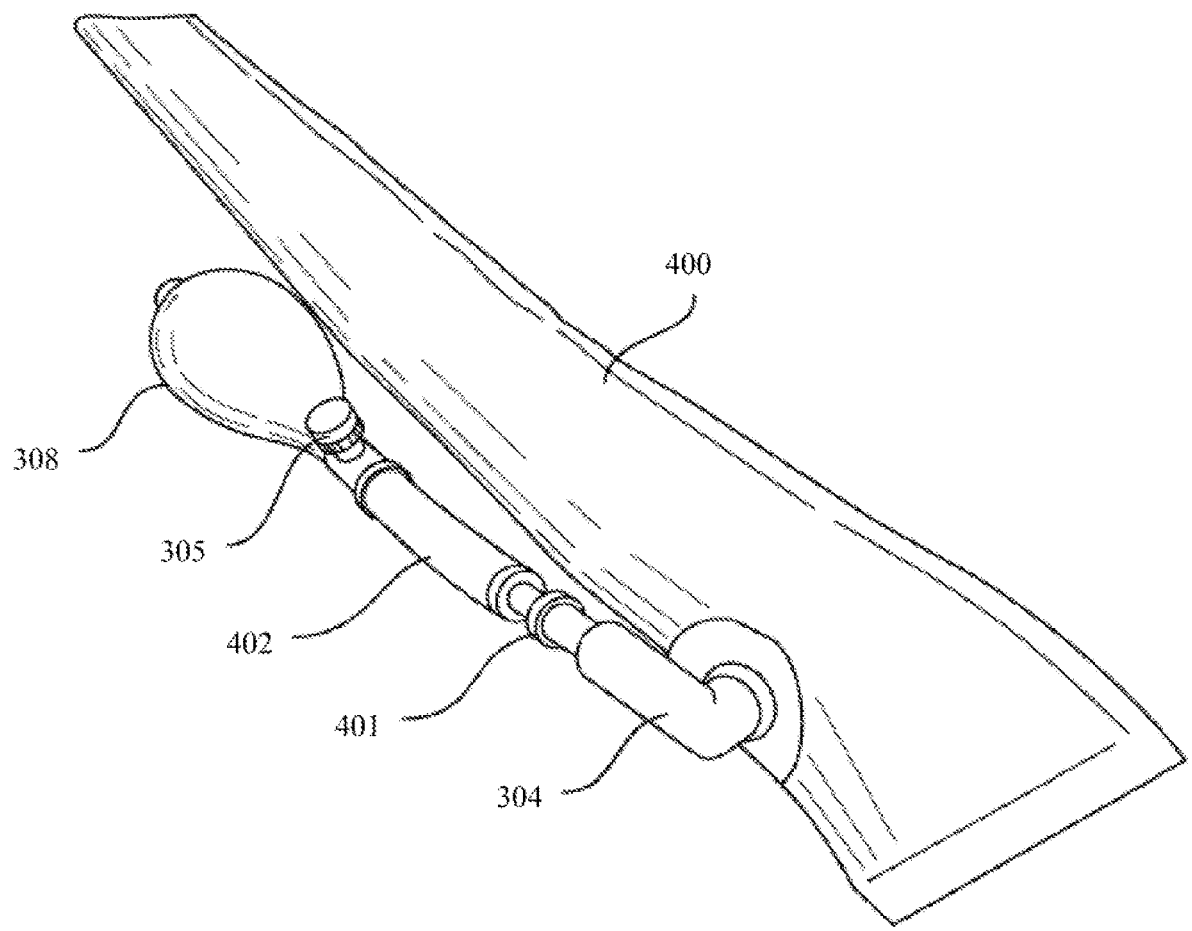
FIG. 15 shows an exemplary bladder that can be positioned within a reservoir chassis of the tourniquet from FIG. 14.
Figure 16A:
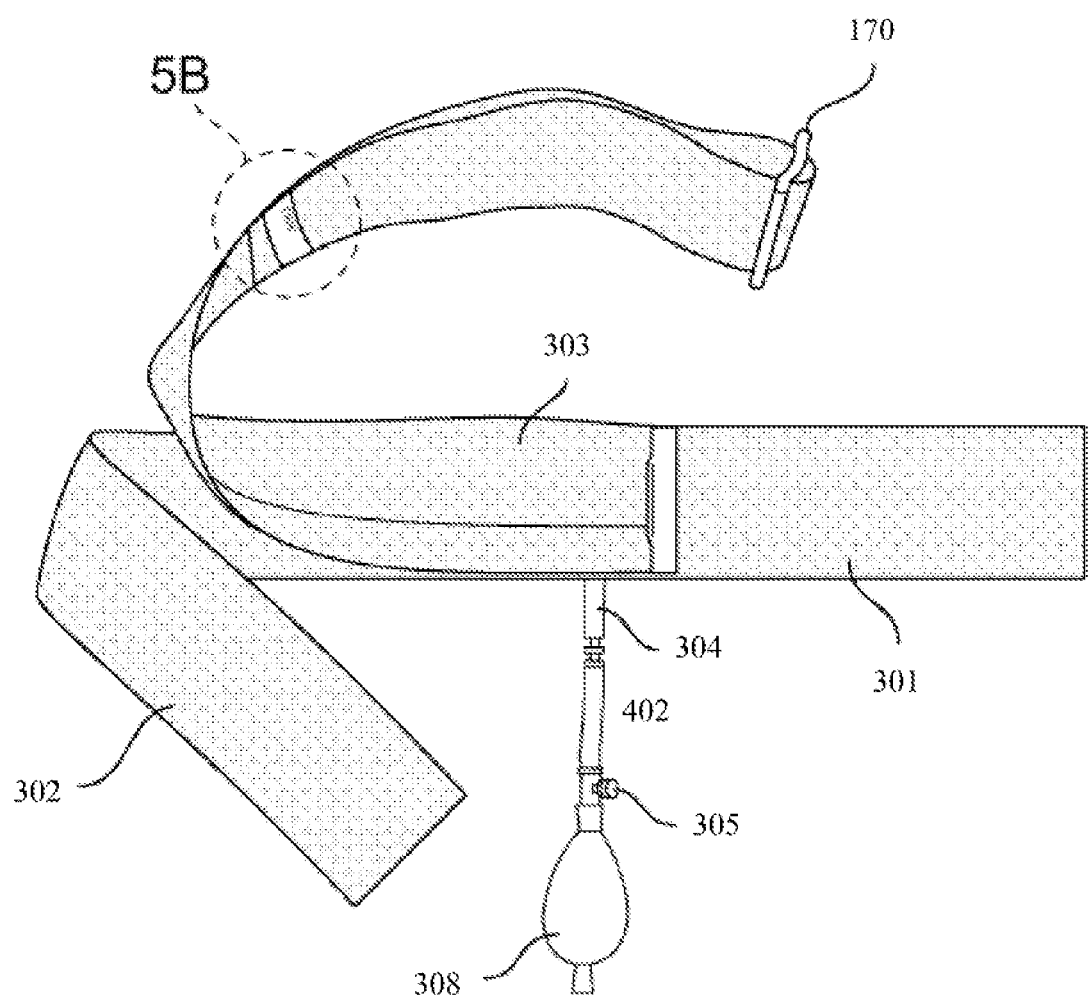
FIG. 16A shows an additional view of a pneumatic tourniquet according to embodiments of the present invention.
Figure 16B:
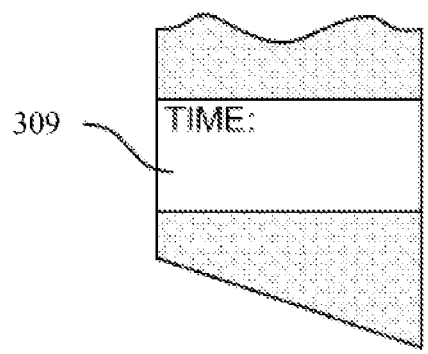
FIG. 16B is a detail view on an enlarged scale of a portion of the tourniquet from FIG. 16A.
Figure 17:
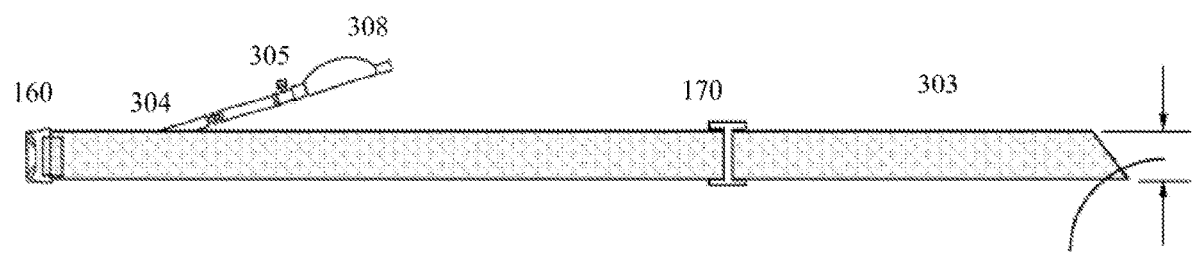
FIG. 17 shows an additional view of a pneumatic tourniquet according to embodiments of the present invention.
Figure 18:
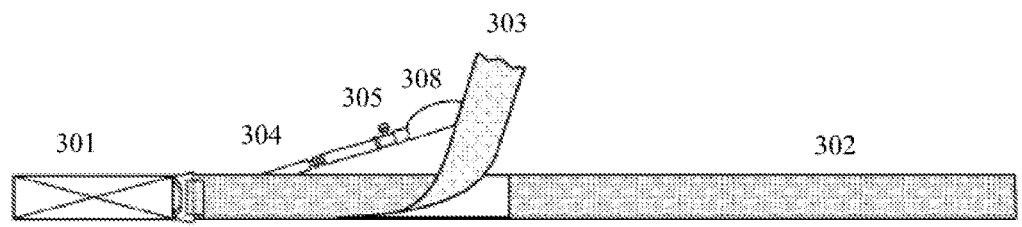
FIG. 18 shows an additional view of a pneumatic tourniquet according to embodiments of the present invention.
Figure 19:
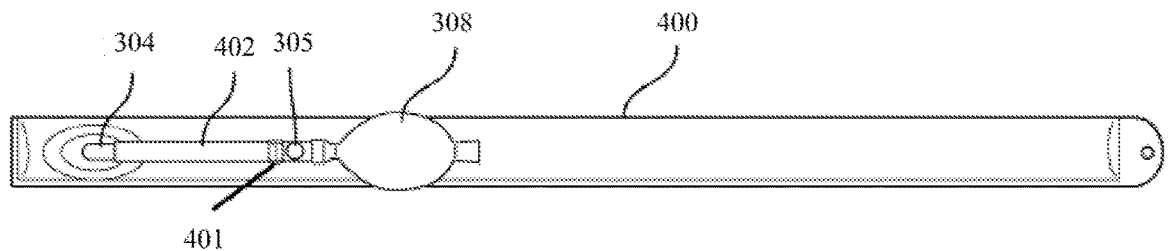
FIG. 19 shows another exemplary bladder that can be positioned within a reservoir chassis of the tourniquet from FIG. 14.

With reference to the figures, and in particular FIG. 14, embodiments of the present invention are directed to a pneumatic tourniquet 300 for restricting a blood flow in a body part, such as an upper or a lower extremity, with the pneumatic tourniquet 300 comprising: (a) a bladder 400 (See FIGS. 15 and 19) sealed from 3 edges to hold and maintain air pressure while being inflated with an inflation pump 308; (b) a reservoir chassis 302 to hold and to protect the bladder 400, with the reservoir chassis 302 including a main section that holds the bladder 400 and a reservoir chassis extension section 301 that extends from the main section but does not hold the bladder 400; (c) a retaining cover 303 that is attached to the reservoir chassis 302 where the main section and the chassis extension section connect, with the retaining cover 303 operable to cover and protect the reservoir chassis 302 (d) a receiver 160 (See also FIG. 4) connected to either the reservoir chassis 302 or the retaining cover 303 proximate to where the retaining cover 303 is attached to the reservoir chassis 302, with the receiver 160 being operable to accept a slider 170 (See also FIG. 5) that is positioned on the retaining cover 303 from any position along the retaining cover 303, and furthermore with the receiver 160 being operable to allow a user to "snap" the slider 170 into place and lift the lip 163 of the receiver 160 to remove the slider 170 upon demand; (e) the slider 170 serves as a friction buckle operable to be placed along any section of the retaining cover 303, with the slider 170 including one round side bar 171 and one square side bar 172 with grippers 175 allowing for free rotation when attached to the receiver 160. In operation, the pneumatic tourniquet (See also FIGS. 16A-18) is operable, via the above described components (a-e), to form a continuous loop around an extremity, such as an arm or a leg, so as to create a circumferential pressure that will restrict blood flow. Such a circumferential pressure is created by and 1) joining the slider 170 and the receiver 160 together and manipulating the retaining cover 303 so as to reduce the circumference of the tourniquet, and 2) pumping air into the bladder 400.

With respect to FIG. 14 (see also FIGS. 16A-18), the reservoir chassis 302 retains and protects the air bladder 400. In some embodiments, the total length is 33 inches and the width is between 2 and 4 inches. In some embodiments, the reservoir chassis 302 includes a section of dual hook and loop fasteners on both sides of the reservoir chassis faces. In other words, the dual hook and loop fasteners are on the side facing "in" and the side facing "out." The tourniquet also includes a retaining cover 303 sized and shaped to overlap the reservoir chassis 302 as a secondary securing mechanism to prevent slippage or pressure reduction. The retaining cover 303 also provides extra protection for the reservoir chassis 302 and bladder 400. The outer surface of the retaining cover 303 includes dual hook and loop fasteners. The reservoir chassis extension 301 does not contain the bladder 400. The reservoir chassis extension 301 is sized and shaped to accommodate larger arm or leg circumferences. In some embodiments, the reservoir chassis 302 and/or the retaining cover 303 further include a blank label 309. The blank label 309 may be used to write the time when the tourniquet is applied or various other relevant notes regarding patient care.

Extending from the bladder 400 (see also FIGS. 15 and 19) is a nipple 304 that connects the bladder to an air pump. In some embodiments, a half bulb inflation pump 308 is used to pump air into the bladder 400 via the nipple 304. In some embodiments, the half bulb inflation pump 308 is latex free and ergonomically designed for ease of use. In some embodiments, the inflation mechanism includes a relief valve 305 to manually control the release of pressure inside the bladder 400. In some embodiments, the inflation includes a metal clamp 401, such as a small brass ring, attached to the connection between the nipple 304 and the relief valve 305 or inflation pump 308.

In more detail, the retaining cover 303 (See FIGS. 14 and 16A-18) includes dual hook and loop (i.e., Velcro) on its exterior surface and a nylon denier on its interior surface (i.e., the surface that faces the bladder 400). Thus, the retaining cover 303 is operable to cover and protect the reservoir chassis 302 and also operable to secure the tourniquet around an extremity. For example, the retaining cover 303 can be positioned in a continuous loop around an extremity by wrapping the retaining cover 303 around the extremity. Next, the slider 170, which is adjustably secured to the retaining cover 303, can be secured to the receiver 160, which is fixably connected to either the reservoir chassis 302 or the retaining cover 303, as previously described. In such an arrangement, the diameter of the continuous loop can be shortened by pulling the retaining strap further through slider 170, thus creating an increased circumferential pressure (i.e., a radial compression). Once a preferred diameter has been obtained, such a diameter can be maintained by folding the retaining cover 303 back upon itself and securing such a position via the hook and loop of the retaining cover 303.

In some embodiments, the bladder 400 (See FIGS. 15 and 19) of the pneumatic tourniquet is formed from a polyurethane plastic material by sealing 3 edges of the plastic material. Furthermore a nipple 304 is attached to the polyurethane plastic and extends therefrom at an approximately 90 degree angle. From the nipple 304, a silicon tube 402 extends a distance and connects with the pump 308, which may, in some embodiments include a semicircle pressure inflation bulb (e.g., an ergonomically designed hemicycle pressure pump). Embodiments in which the pump 308 is a semicircular face may be preferable in instances when the tourniquet is required to be packaged in a small space. In certain embodiments, the bladder 400 is preferred to hold at least 450 mmHg of pressure, so as to be sufficient to stop blood flow and hemorrhage in an extremity. In other embodiments, the bladder 400 will hold more or less than 450 mmHg. In some embodiments, the bladder 400 will be approximately 25 inches in length, so as to be sufficient for use with human extremities (i.e., arms and legs) that have sizes within the 5th to 95th percentile. Regardless, embodiments of the present invention contemplate bladder lengths that are more or less than 25 inches. Furthermore, in some embodiments, the width of the bladder will be approximately 1.5 inches, which proves for a broad pressure base that can be applied to an extremity. However, it is understood that widths more or less than 1.5 inches may be used in some embodiments. The bladder 400 will, in some embodiments, also include a relief valve 305 that provides for a manual or automatic release of air pressure within the bladder 400.

Embodiments of the present invention provide for the reservoir chassis 302 (See FIGS. 14 and 16A-18) to protect the bladder 400 (See also FIGS. 15 and 19) from environmental damages that may occur during transportation or use of the tourniquet. In some embodiments, the reservoir chassis 302 will be formed in a coyote brown color to uniquely identify a first application of the tourniquet over the circumference of the damaged extremity. In some embodiments, a length of the reservoir chassis 302 is approximately 33 inches. However, in other embodiments, the chassis 302 may be more or less than 33 inches. With the total length of the reservoir chassis 302 being 33 inches, some embodiments provide for the main section to be about 25 inches length (or at least long enough to hold the bladder 400), and the extension section 301 to be about 8 inches in length. In some embodiments, the extension section 301 is included so as to provide for the comfortable placement of the tourniquet onto larger sized extremities. Further, some embodiments provide for two sections of approximately 16 inches of hook and loop to be positioned on an interior and exterior surface of the reservoir chassis. In particular, a first section of hook and loop is positioned on the exterior surface of the reservoir chassis 302 adjacent to an end of the reservoir chassis 302 that is opposite the extension section 301. In some embodiments, more or less than 16 inches of hook and loop will be added to the reservoir chassis 302. In certain additional embodiments, the interior surface of the reservoir chassis 302 will have a section of hook and loop thereon, with the section covering the extension section 301 and extending from the extension section 301 along a portion of the main section. In such embodiments, the main section of the reservoir chassis 302 can be wrapped around an extremity and can be secured in place by connecting the dual hook and loop on the outer surface of the main section with the dual hook and loop on the interior surface of the extension section 301. As such, the tourniquet can be initially positioned over and secured to an extremity until the slider 170 can be connected to the receiver 160 and the retaining cover 303 tightened and secured in a preferred position. Once the retaining cover 303 is tightened and secured in a preferred position, the bladder 400 can be pumped up and filled with air to create the intended circumferential pressure to stop hemorrhaging and blood loss.

In some embodiments, the pneumatic tourniquet includes the retaining cover 303 (See FIGS. 14 and 16A-18) which is sewn with nylon coated fabric and dual hook and loop, as previously described. In some embodiments, the retaining cover 303 is approximately 39 inches length. In other embodiments, the retaining cover 303 may be more or less than 39 inches. The retaining cover 303 preferably overlaps the reservoir chassis 302 as a secondary securing mechanism to prevent any slippage and provides extra protection. The retaining cover 303 includes a time label 309 which is comprised of a clothing label and is inserted on an end of the cover to write the time when application of the tourniquet is made.

Additional embodiments of the present invention include a tourniquet (See FIGS. 14 and 16A-18) that is operable for restricting a flow of blood in a body part, such an upper or a lower extremity, with such a tourniquet comprising: (a) a bladder 400 (See FIGS. 15 and 19) placed into a reservoir chassis 302, with the reservoir chassis 302 including a main section that holds the bladder 400 and an extension section 301 connected to said main section; (b) a retaining cover 303 attached to the reservoir chassis 302 at a position adjacent to where the main section of the reservoir chassis 302 connects to the extension section 301; (c) a receiver 160 (See also FIG. 4) joined with the retaining cover 303 or the reservoir chassis 302 adjacent to the position where the retaining cover 303 is attached to the reservoir chassis 302; and (c) a slider 170 (See also FIG. 5) attached to the retaining cover 303 for quick application to the receiver 160. In such embodiments, when the tourniquet is placed onto the damaged circumference of the extremity, the slider 170 can be attached to the receiver 160 and then the retaining cover 303 can be adjusted to a preferred position so as to create a circumferential pressure. Furthermore, the retaining cover 303 can be secured in such a position by folding an end of the retaining cover 303 back on itself such that the dual hook and loop of the retaining cover 303 secures the retaining cover 303 in place.

As illustrated in FIG. 4, the receiver 160 includes a hook-shaped catch 161 that the round side bar 171 of the slider 170 (See FIG. 5) can be placed into or removed from by the user on demand through application of the receiver flange 162. A lip portion 163 of the receiver is the narrower portion of the receiver 160 and facilitates ease of placement for the round side bar 171 of the slider 170, and the bar locks the hook slider into place.

With respect to FIG. 4, in some embodiments, the hook-shaped catch 161 (or slider niche) is sized and shaped to mate with and receive the slider 170 and lock the slider 170 securely in place. The receiver flange 162 guides and provides an easy placement for the slider 170 which locks the retaining cover 303 in place. The flange 162 slopes upward to facility placement. The lip 163 is a narrower part of the receiver 160 to provide an easy placement with the receiver flange 162 for the slider 170. A bar 164 hangs down from the lip 163. The bar 164 supports locking of the hook slide and prevents unintentional displacement (dislodging) of the slider 170 from the receiver 160. The bar 164 allows the slider 170 to "snap" or audibly "click" when the slider 170 and receiver 160 are properly mated. A supporter 166 is a thicker portion of the receiver 160 that structurally supports the receiver slot 165. The receiver slot 165 is a space for a receiver holder to connect the receiver 160 to the retaining cover 303 or reservoir chassis 302.

With reference to FIG. 5, the slider 170 functions as a friction buckle that is operable to be placed anywhere on the retaining cover 303. The square side bar 172 of the slider 170 with protruding grippers 175 facilitates friction when the round side bar 501 is placed into the receiver 160 (See FIG. 4). As such, the slider 170 reduces slippage, yet allows excess slack to be removed from the diameter of the circumferential tourniquet body upon demand from the user with an upward pulling motion of the retaining cover 303. Furthermore, the retaining cover 303 can be pre-routed through the slider 170, thus avoiding the necessity to route the retaining cover 303 through the slider 170 during use.

Avoiding the need to route the retaining cover 303 through the slider 170 is one of the major advantages of the present inventive concept. Under duress or in emergency situations, many users experience compromised fine motor skills. One example of a prior art tourniquet requires the user to route a strap through two specific slots in a buckle in a specific order. Studies showed that in a large number of failures of the prior art tourniquet resulting in death, the user had routed the strap through the buckle incorrectly. The present inventive concept addresses this known problem by adding a feature that makes it difficult or impossible to pull the terminal end through the buckle. In some embodiments, the terminal end of the retaining cover 303 is folded over on to itself. This creates a "stop" that discourages the user from pulling the retaining cover 303 out of the slider 170. In some embodiments, the folded-over terminal end is sewn such that it cannot be unfolded. In some embodiments, the folded-over terminal end includes an insert, preferably plastic, to increase the size of the "stop" and further decreasing the ability of the user to pull the terminal end through the slider 170.

With respect to FIG. 5, in some embodiments, the slider 170 includes a round edge 171 (or round side bar). The round side bar 171 is sized and shaped to interface with the receiver 160. The round side bar 171 is sized and shaped to allow for articulation when mated with the receiver 160. The slider 170 further includes a frame 172 (or square side bar). The square side bar 172 gives support, structure and shape to the slider 170. In some embodiments, the slider 170 will be a distinctive color to easily and quickly visually distinguish the slider's position relative to the retaining cover 303. For example, in some embodiments, the slider 170 is coyote brown. In some embodiments, the slider 170 includes a slider friction bar 173. The slider friction bar 173 provides friction and inhibits the release of tension when the tourniquet is applied. The friction bar 173 is positioned higher than the side bars 171 and 172. The friction bar 173 is sized and shaped to lock the slider 170 in position when the tourniquet is applied. The slider 170 further includes slider gaps 174. The retaining cover 303 is routed through the slider gaps 174 with dual hook and loop fasteners on the retaining cover 303 side that faces toward the slider friction bar 173. The square side bar 172 of the slider 170 also includes grippers 175. The grippers 175 facilitate friction when the round slider bar 171 is placed into the receiver 160. This stops slippage, yet allows excess slack to be removed from the retaining cover 303 continuous loop upon demand with an upward pulling motion of the retaining cover 303.

Together, the slider 170 (See FIG. 5) and the receiver 160 (See FIG. 4) function as a buckle, so as to create a continuous loop of the tourniquet. Adjustments can be made, via the slider 170, for shortening or lengthening the continuous loop once applied, and/or the slider 170 can be attached or detached from the receiver 160 to facilitate ease of application by the user.

In some embodiments, certain portions of the tourniquet, such as the reservoir chassis 302 and the retaining cover 303 may be made from various types of elastic and/or inelastic flexible material, such as woven fabric, vinyl, leather, neoprene, nylon, etc. Additionally, other components of the tourniquet (e.g., receiver 160 and slider 170) may be made from rigid or semi-rigid materials, such as various types plastics, metals, or the like. Furthermore, portions of the bladder 400, including the bladder 400 itself or the nipple 304, tubing 402, and pump 308, may be made from various materials that are flexible but operable to securely hold fluid therein, such as neoprene, polyurethane, other plastic, or other similar material.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall therebetween. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A tourniquet comprising:
a tourniquet body having a length sufficient to encircle a limb; and
a carriage engaged with the tourniquet body,
wherein the tourniquet is moveable from an unconstricted configuration towards a constricted configuration,
wherein the carriage is formed at least partially from a first material, the first material being a rigid or semi-rigid material,
wherein the carriage comprises a base plate and a first bridge with a horizontal portion displaced radially outboard from the base plate,
wherein the carriage further comprises a second bridge, said first and second bridges being positioned at respective first and second ends of the carriage, the first and second bridges defining respective first and second niches,
wherein the tourniquet body extends through the first and second niches,
wherein the first and second bridges are configured to allow the tourniquet body to move efficiently through respective first and second niches when moving the tourniquet from the unconstricted configuration towards the constricted configuration, and
wherein the first bridge comprises opposed radial portions extending between the base plate and the horizontal portion of the first bridge, thereby defining the first niche.

2. The tourniquet of claim 1, wherein the carriage is of uniform construction such that the carriage is formed entirely from the first material.

3. The tourniquet of claim 1, wherein the base plate of the carriage defines a gradual curve such that the carriage is configured to engage with the limb.

4. The tourniquet of claim 3, wherein the carriage is configured to conform to extremities of varying sizes such that the tourniquet is configured to be used on human extremities that are sized between the 5th and 95th percentile.

5. The tourniquet of claim 1, further comprising a torsion bar, wherein the first bridge comprises a torsion bar retainer that is configured to engage with the torsion bar so as to retain the tourniquet in the constricted configuration.

6. A tourniquet comprising:
a tourniquet body having a length sufficient to encircle a limb;
a carriage engaged with the tourniquet body; and
a tightening strap attached to the tourniquet body at each of opposed first and second ends of the tightening strap,
wherein the tourniquet is moveable from an unconstricted configuration towards a constricted configuration,
wherein the carriage is formed at least partially from a first material, the first material being a rigid or semi-rigid material,
wherein the carriage comprises a base plate and a first bridge with a horizontal portion displaced radially outboard from the base plate,
wherein moving the tourniquet from the unconstricted configuration to the constricted configuration comprises pulling the first and second ends of the tightening strap towards each other such that a first portion of the tourniquet body bunches together while a second portion of the tourniquet body is caused to constrict around the limb,
wherein the first portion of the tourniquet body extends over exterior side of the base plate, and
wherein the base plate of the carriage has an interior side positioned facing toward the limb and the exterior side positioned facing away from the limb, the tourniquet body extending over the exterior side of the base plate.

7. The tourniquet of claim 6, further comprising a torsion bar defining a slot, wherein the tightening strap is routed through the slot of the torsion bar.

8. The tourniquet of claim 7, wherein twisting of the torsion bar causes the tightening strap to twist, thereby causing the first portion of the tourniquet body to bunch over the base plate of the carriage.

9. A tourniquet comprising:
a tourniquet body having a length sufficient to encircle a limb; and
a carriage engaged with the tourniquet body,
wherein the tourniquet is moveable from an unconstricted configuration towards a constricted configuration,
wherein the carriage is formed at least partially from a first material, the first material being a rigid or semi-rigid material,
wherein the carriage comprises a base plate and a first bridge with a horizontal portion displaced radially outboard from the base plate, and
wherein the first bridge is positioned at a first end of the carriage, the first bridge further comprising opposed vertical portions extending between the base plate and the horizontal portion of the bridge, thereby defining a first niche.

10. The tourniquet of claim 9, wherein the tourniquet body extends through the first niche such that the first bridge inhibits radial movement away from the base plate while allowing the tourniquet body to move efficiently through the first niche.

* * * * *